United States Patent [19]

Hidaka et al.

[11] Patent Number: 4,525,589
[45] Date of Patent: Jun. 25, 1985

[54] ISOQUINOLINESULFONYL DERIVATIVES

[75] Inventors: Hiroyoshi Hidaka, 799-25, Kannonji-cho, Tsu-shi, Mie-ken; Takanori Sone, Nobeoka; Yasuharu Sasaki, Nobeoka; Taisuke Sugihara, Nobeoka, all of Japan

[73] Assignees: Asahi Kasei Kogyo Kabushiki Kaisha; Hiroyoshi Hidaka, both of Japan

[21] Appl. No.: 572,418

[22] Filed: Jan. 20, 1984

Related U.S. Application Data

[62] Division of Ser. No. 357,770, Mar. 12, 1982, Pat. No. 4,456,757.

[30] Foreign Application Priority Data

Mar. 20, 1981 [JP]  Japan ............................. 56-399550
Jun. 1, 1981 [JP]   Japan ............................. 56-82559
Jan. 12, 1982 [JP]  Japan ............................. 57-2229
Jan. 14, 1982 [JP]  Japan ............................. 57-3291

[51] Int. Cl.³ .......................................... C07D 413/12
[52] U.S. Cl. .................................. 544/128; 544/363; 546/139; 546/149; 260/244.4
[58] Field of Search ................. 544/128; 546/139; 260/244.4

[56] References Cited

U.S. PATENT DOCUMENTS 3,845,662 10/1974 Holland ............................... 544/128
4,060,522 11/1977 Kindscher et al. ................... 544/128
4,223,137  9/1980 Yoshizaki et al. ................... 544/128

Primary Examiner—Glennon H. Hollrah
Assistant Examiner—James H. Turnipseed
Attorney, Agent, or Firm—Finnegan, Henderson, Farabow, Garrett & Dunner

[57] ABSTRACT

A 5-isoquinolinesulfonyl derivative of Formula (I):

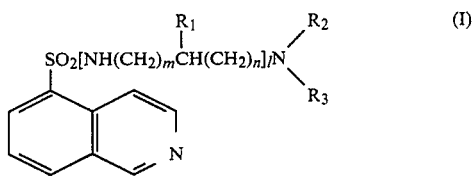

wherein
$l$ is zero or one;
$m$ and $n$ each is an integer of one to nine;
$m+n$ is an integer of at least one
$R_1$ is a hydrogen atom, a $C_{1-10}$ alkyl group, a $C_{5-6}$ cycloalkyl group or an aryl group; or
$R_2$ and $R_3$ each is a hydrogen atom, a $C_{1-10}$ alkyl group, a $C_{5-6}$ cycloalkyl group, an aryl group or an aralkyl group;
$R_2$ and $R_3$ are $C_{1-6}$ alkylene groups and linked directly or through an oxygen atom to form a 5- to 7-membered heterocyclic ring with the adjacent nitrogen atom; or the

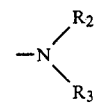

group is a

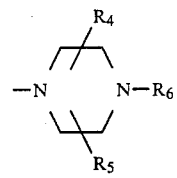

group wherein $R_4$ and $R_5$ each is a hydrogen atom, a $C_{1-10}$ alkyl group, an aryl group or an aralkyl group and $R_6$ is a hydrogen atom, a $C_{1-10}$ alkyl group, an aryl group, an aralkyl group, a benzoyl group, a cinnamyl group, a cinnamoyl group, a furoyl group or a

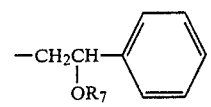

group wherein $R_7$ is a $C_{1-8}$ alkyl group;
and the pharmaceutically acceptable salt thereof; and a process for the preparation thereof. The compounds of this invention have a relaxatory action for vascular smooth muscle and are useful as a vasodilator and a hypotensor.

8 Claims, No Drawings

ISOQUINOLINESULFONYL DERIVATIVES

This is a division of application Ser. No. 357,770, filed Mar. 12, 1982, now U.S. Pat. No. 4,456,757.

BACKGROUND OF THE INVENTION

Field of the Invention

This invention relates to novel isoquinolinesulfonyl derivatives which possess a relaxatory action for vascular smooth muscle and are useful as a vasodilator and a hypotensor, and a process for the preparation thereof.

SUMMARY OF THE INVENTION

According to the present invention in one embodiment there is provided an isoquinoline derivative of Formula (I):

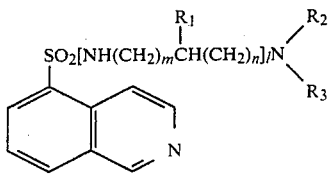

wherein
l is zero or one;
m and n each is zero or an integer of one to nine;
m+n is an integer of at least one;
$R_1$ is a hydrogen atom, a $C_{1-10}$ alkyl group, a $C_{5-6}$ cycloalkyl group or an aryl group;
$R_2$ and $R_3$ each is a hydrogen atom, a $C_{1-10}$ alkyl group, a $C_{5-6}$ cycloalkyl group, an aryl group or an aralkyl group;
$R_2$ and $R_3$ may be $C_{1-6}$ alkylene groups and linked directly or through an oxygen atom to form a 5- to 7-membered heterocyclic ring with the adjacent nitrogen atom; or
the

group is a

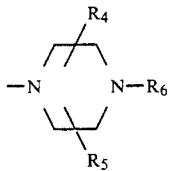

group wherein $R_4$ and $R_5$ each is a hydrogen atom, a $C_{1-10}$ alkyl group, an aryl group or an aralkyl group and $R_6$ is a hydrogen atom, a $C_{1-10}$ alkyl group, an aryl group, an aralkyl group, a benzoyl group, a cinnamyl group, a cinnamoyl group, a furoyl group or a

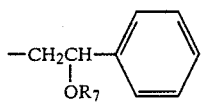

group wherein $R_7$ is a $C_{1-8}$ alkyl group;
and the pharmaceutically acceptable acid addition salt thereof.

The present invention in another embodiment provides a process of preparing th above described isoquinolinesulfonyl derivative.

DETAILED DESCRIPTION OF THE INVENTION

Exemplary $R_1$ groups in Formula (I) include a hydrogen atom; $C_{1-10}$ alkyl groups, preferably $C_{1-6}$ alkyl groups, such as methyl, ethyl, n-propyl, isopropyl, n-butyl, isobutyl, sec-butyl, tert-butyl, n-pentyl, n-hexyl, n-heptyl, n-octyl, n-nonyl and decyl; $C_{5-6}$ cycloalkyl groups such as cyclopentyl and cyclohexyl; and aryl groups such as phenyl. The $R_2$ and $R_3$ groups in Formula (I) may be the same or different and exemplary $R_2$ and $R_3$ groups include a hydrogen atom; $C_{1-10}$ alkyl groups, preferably $C_{1-8}$ alkyl groups such as methyl, ethyl, n-propyl, isopropyl, n-butyl, isobutyl, sec-butyl, tert-butyl, n-pentyl, isopentyl, n-hexyl, n-heptyl, n-octyl, n-nonyl and n-decyl; $C_{5-6}$ cycloalkyl groups such as cyclopentyl and cyclohexyl; aryl groups such as phenyl; and aralkyl groups such as benzyl. Exemplary 5- to 7-membered heterocyclic rings formed by linking $R_2$ and $R_3$ directly or through an oxygen atom together with the adjacent nitrogen atom include 1-pyrrolidinyl, piperidino, homopiperidino and morpholino groups. Preferred

groups include amino, methylamino, ethylamino, n-propylamino, isopropylamino, n-butylamino, isobutylamino, n-hexylamino, cyclohexylamino, dimethylamino, diethylamino, di-n-butylamino, N-methyl-N-cyclopentylamino, N-methyl-N-cyclohexylamino, N-methyl-N-phenylamino, N-methyl-N-benzylamino, N-ethyl-N-benzylamino, N-isopropyl-N-benzylamino, 1-pyrrolidinyl, piperidino, homopiperidino and morpholino groups. The

group may also be a

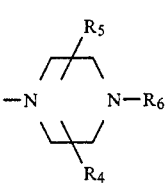

group. The $R_2$ and $R_3$ groups may be the same or different and exemplary $R_4$ and $R_5$ groups include a hydrogen atom; $C_{1-10}$ alkyl groups, preferably $C_{1-6}$ alkyl groups, such as methyl, ethyl, n-propyl, isopropyl, n-butyl, isobutyl, n-pentyl, isopentyl, n-hexyl, n-heptyl, n-octyl, n-nonyl and n-decyl; $C_{5-6}$ cycloalkyl groups such as cyclopentyl and cyclohexyl; aryl group such as phenyl;

and aralkyl groups such as benzyl, α-phenethyl and β-phenethyl. Exemplary R₆ groups include a hydrogen atom; C₁₋₁₀ alkyl groups, preferably C₁₋₆ alkyl groups, such as methyl, ethyl, n-propyl, isopropyl, n-butyl, isobutyl, n-pentyl, isopentyl, n-hexyl, n-heptyl, n-octyl, n-nonyl and n-decyl; aryl groups such as phenyl; aralkyl groups such as benzyl, α-phenethyl and β-phenethyl; a benzoyl group; a cinnamyl group; a cinnamoyl group; a furoyl group; a

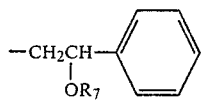

group wherein R₇ is a C₁₋₈ alkyl group, preferably a C₁₋₄ alkyl group, such as methyl, ethyl, n-propyl, isopropyl, n-butyl, isobutyl, n-pentyl, n-hexyl, n-heptyl and n-octyl groups. Preferred

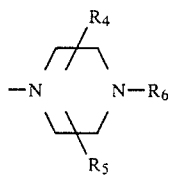

groups include piperazino, 2-methylpiperazino, 2-ethylpiperazino, 3-ethylpiperazino, 3-isopropylpiperazino, 3-isobutylpiperazino, 2-phenylpiperazino, 3-phenylpiperazino, 3-benzylpiperazino, 2,3-dimethylpiperazino, 2,5-dimethylpiperazino, 3,5-dimethylpiperazino, 2,6-dimethylpiperazino, 2-methyl-5-ethylpiperazino, 2-methyl-5-n-propylpiperazino, 2-methyl-5-isopropylpiperazino, 2-methyl-5-isobutylpiperazino, 2-methyl-5-phenylpiperazino, 2-methyl-5-benzylpiperazino, 2,5-diethylpiperazino, 2-ethyl-5-n-butylpiperazino, 4-methylpiperazino, 4-ethylpiperazino, 4-n-propylpiperazino, 4-isobutylpiperazino, 4-n-hexylpiperazino, 4-phenylpiperazino, 4-benzylpiperazino, 4-phenethylpiperazino, 4-benzoylpiperazino, 4-cinnamylpiperazino, 4-cinnamoylpiperazino, 4-furoylpiperazino, 4-(2-methoxy-2-phenethyl)piperazino and 4-(2-ethoxy-2-phenethyl)piperazino groups.

Preferred embodiments are as follows:

(a) A compound of Formula (XIII)

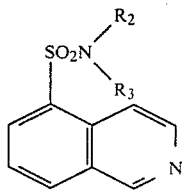

(XIII)

wherein
R₂ and R₃ each is a hydrogen atom, a C₁₋₈ alkyl group, a phenyl group or a benzyl group, and when one of R₂ and R₃ is a hydrogen atom, the other is not a hydrogen atom; or
R₂ and R₃ are C₁₋₆ alkylene groups and linked directly or through an oxygen atom to form a 5- to 7-membered heterocyclic ring together with the adjacent nitrogen atom; or
the

group is a

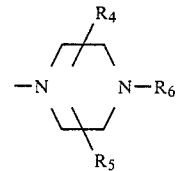

group wherein R₄ and R₅ each is a hydrogen atom, a C₁₋₆ alkyl group, a phenyl group or a benzyl group and R₆ is a hydrogen atom, a C₁₋₆ alkyl group, a phenyl group, a benzyl group, a phenethyl group, a benzoyl group, a cinnamyl group, a cinnamoyl group, a furoyl group or a

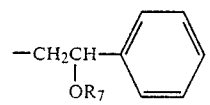

group wherein R₇ is a C₁₋₄ alkyl group;
and pharmaceutically acceptable acid addition salts thereof, i.e., a compound of Formula (I) wherein l is zero.

(b) The compound of (a), wherein R₂ is a hydrogen atom or a C₁₋₆ alkyl group and R₃ is a C₁₋₆ alkyl group.

(c) The compound of (a), wherein the

group is a 1-pyrrolidinyl group, a piperidino group or a morpholino group.

(d) The compound of (a), wherein the

group is a

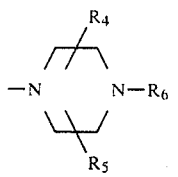

group wherein R₆ is a hydrogen atom and R₄ and R₅ each is a hydrogen atom, a C₁₋₆ alkyl group, a phenyl group or a benzyl group.

(e) The compound of (d), wherein R₆, R₄ and R₅ are hydrogen atoms.

(f) The compound of (d), wherein $R_4$ is a hydrogen atom or a $C_{1-6}$ alkyl group and $R_5$ is a $C_{1-6}$ alkyl group, a phenyl group or a benzyl group.

(g) The compound of (a), wherein the

group is a

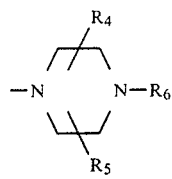

group wherein $R_4$ and $R_5$ are hydrogen atoms and $R_6$ is a $C_{1-6}$ alkyl group, a phenyl group, a benzyl group, a phenethyl group, a benzoyl group, a cinnamyl group, a cinnamoyl group, a furoyl group or a

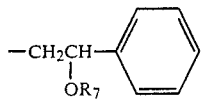

group wherein $R_7$ is a $C_{1-4}$ alkyl group.

(h) The compound of (g), wherein $R_6$ is a $C_{1-6}$ alkyl group.

(i) The compound of (g), wherein $R_6$ is a phenyl group, a benzyl group, a phenethyl group, a benzoyl group, a cinnamyl group, a cinnamoyl group or a furoyl group.

(j) The compound of (g), wherein $R_6$ is a

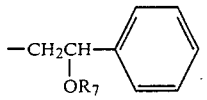

group wherein $R_7$ is a $C_{1-4}$ alkyl group.

(k) A compound of Formula (XIV):

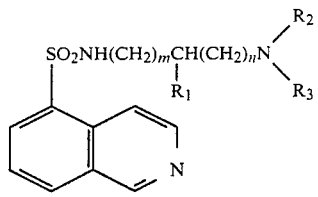

wherein
m and n each is zero or an integer of one to nine;
m+n is an integer of one to nine;
$R_1$ is a hydrogen atom, a $C_{1-6}$ alkyl group or a phenyl group;
$R_2$ and $R_3$ each is a hydrogen atom, a $C_{1-8}$ alkyl group, a $C_{5-6}$ cycloalkyl group, a phenyl group or a benzyl group; or
$R_2$ and $R_3$ are $C_{1-6}$ alkylene groups and linked directly or through an oxygen atom to form a 5- to 7-membered heterocyclic ring together with the adjacent nitrogen atom; or
the

group is a

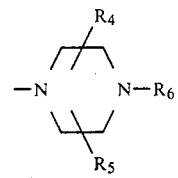

group wherein $R_4$ and $R_5$ each is a hydrogen atom, a $C_{1-6}$ alkyl group, a phenyl group or a benzyl group and $R_6$ is a hydrogen atom, a $C_{1-6}$ alkyl group, a phenyl group, a benzyl group, a phenethyl group, a benzoyl group, a cinnamyl group, a cinnamoyl group, a furoyl group or a

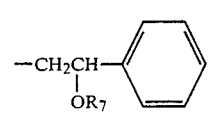

group wherein $R_7$ is a $C_{1-4}$ alkyl group;
and pharmaceutically acceptable acid addition salts thereof, i.e., a compound of Formula (I), wherein l is one.

(l) The compound of (k), wherein m and n each is zero or an integer of one to nine, m+n is an integer of one to nine and $R_1$, $R_2$ and $R_3$ are hydrogen atoms.

(m) The compound of (k), wherein m and n each is zero or one, m+n is one, $R_2$ and $R_3$ are hydrogen atoms and $R_1$ is a $C_{1-6}$ alkyl group or a phenyl group.

(n) The compound of (k), wherein m and n each is zero or an integer of one to two, m+n is one or two, $R_1$ is a hydrogen atom, $R_2$ is a hydrogen atom or a $C_{1-4}$ alkyl group and $R_3$ is a $C_{1-6}$ alkyl group, a $C_{5-6}$ cycloalkyl group, a phenyl group or a benzyl group.

(o) The compound of (k), wherein m and n each is zero or an integer of one to two, m+n is one or two, $R_1$ is a hydrogen atom and $R_2$ and $R_3$ form together with the adjacent nitrogen atom a piperidino group or a morpholino group.

Exemplary isoquinolinesulfonyl derivatives of this invention include:

(1) N-(2-aminoethyl)-5-isoquinolinesulfonamide referred to as "Compound (1)";

(2) N-(3-aminopropyl)-5-isoquinolinesulfonamide referred to as "Compound (2)";

(3) N-(4-aminobutyl)-5-isoquinolinesulfonamide referred to as "Compound (3)";

(4) N-(6-aminohexyl)-5-isoquinolinesulfonamide referred to as "Compound (4)";

(5) N-(10-aminodecyl)-5-isoquinolinesulfonamide referred to as "Compound (5)";

(6) N-(2-amino-1-methylethyl)-5-isoquinolinesulfonamide referred to as "Compound (6)";

(7) N-(1-aminomethylpropyl)-5-isoquinolinesulfonamide referred to as "Compound (7)";

(8) N-(1-aminomethylpentyl)-5-isoquinolinesulfonamide referred to as "Compound (8)";
(9) N-(2-aminopropyl)-5-isoquinolinesulfonamide referred to as "Compound (9)";
(10) N-(2-aminobutyl)-5-isoquinolinesulfonamide referred to as "Compound (10)";
(11) N-(2-amino-3-methylbutyl)-5-isoquinolinesulfonamide referred to as "Compound (11)";
(12) N-(2-amino-1-phenylethyl)-5-isoquinolinesulfonamide referred to as "Compound (12)";
(13) N-(2-amino-2-phenylethyl)-5-isoquinolinesulfonamide referred to as "Compound (13)";
(14) N-(2-methylaminoethyl)-5-isoquinolinesulfonamide referred to as "Compound (14)";
(15) N-(2-ethylaminoethyl)-5-isoqinolinesulfonamide referred to as "Compound (15)";
(16) N-(2-isopropylaminoethyl)-5-isoquinolinesulfonamide referred to as "Compound (16)";
(17) N-(3-dimethylaminopropyl)-5-isoquinolinesulfonamide referred to as "Compound (17)";
(18) N-(3-diethylaminopropyl)-5-isoquinolinesulfonamide referred to as "Compound (18)";
(19) N-(3-di-n-butylaminopropyl)-5-isoquinolinesulfonamide referred to as "Compound (19)";
(20) N-(3-piperidinopropyl)-5-isoquinolinesulfonamide referred to as "Compound (20)";
(21) N-(3-morpholinopropyl)-5-isoquinolinesulfonamide referred to as "Compound (21)";
(22) N-[3-(N-methyl-N-cyclohexylamino)propyl]-5-isoquinolinesulfonamide referred to as "Compound (22)";
(23) N-[3-(N-methyl-N-phenylamino)propyl]-5-isoquinolinesulfonamide referred to as "Compound (23)";
(24) N-[3-(N-methyl-N-benzylamino)propyl]-5-isoquinolinesulfonamide referred to as "Compound (24)";
(25) N-methyl-5-isoquinolinesulfonamide referred to as "Compound (25)";
(26) N-ethyl-5-isoquinolinesulfonamide referred to as "Compound (26)";
(27) N-n-Butyl-5-isoquinolinesulfonamide referred to as "Compound (27)";
(28) N-isobutyl-5-isoquinolinesulfonamide referred to as "Compound (28)";
(29) N,N-dimethyl-5-isoquinolinesulfonamide referred to as "Compound (29)";
(30) N,N-diethyl-5-isoquinolinesulfonamide referred to as "Compound (30)";
(31) N,N-di-n-butyl-5-isoquinolinesulfonamide referred to as "Compound (31)";
(32) 1-(5-isoquinolinesulfonyl)piperidine referred to as "Compound (32)";
(33) 4-(5-isoquinolinesulfonyl)pyrrolidine referred to as "Compound (33)";
(34) 1-(5-isoquinolinesulfonyl)morpholine referred to as "Compound (34)";
(35) 1-(5-isoquinolinesulfonyl)piperazine referred to as "Compound (35)";
(36) 1-(5-isoquinolinesulfonyl)-4-methylpiperazine referred to as "Compound (36)";
(37) 1-(5-isoquinolinesulfonyl)-3-methylpiperazine referred to as "Compound (37)";
(38) 1-(5-isoquinolinesulfonyl)-2-methylpiperazine referred to as "Compound (38)";
(39) 1-(5-isoquinolinesulfonyl)-3,5-dimethylpiperazine referred to as "Compound (39)";
(40) 1-(5-isoquinolinesulfonyl)-2,5-dimethylpiperazine referred to as "Compound (40)";
(41) 1-(5-isoquinolinesulfonyl)-2,3-dimethylpiperazine referred to as "Compound (41)";
(42) 1-(5-isoquinolinesulfonyl)-4-ethylpiperazine referred to as "Compound (42)";
(43) 1-(5-isoquinolinesulfonyl)-3-ethylpiperazine referred to as "Compound (43)";
(44) 1-(5-isoquinolinesulfonyl)-4-n-propylpiperazine referred to as "Compound (44)";
(45) 1-(5-isoquinolinesulfonyl)-3-isopropylpiperazine referred to as "Compound (45)";
(46) 1-(5-isoquinolinesulfonyl)-3-isobutylpiperazine referred to as "Compound (46)";
(47) 1-(5-isoquinolinesulfonyl)-4-isobutylpiperazine referred to as "Compound (47)";
(48) 1-(5-isoquinolinesulfonyl)-2,5-diethylpiperazine referred to as "Compound (48)";
(49) 1-(5-isoquinolinesulfonyl)-2-methyl-5-isobutylpiperazine referred to as "Compound (49)";
(50) 1-(5-isoquinolinesulfonyl)-2-methyl-5-benzylpiperazine referred to as "Compound (50)";
(51) 1-(5-isoquinolinesulfonyl)-4-hexylpiperazine referred to as "Compound (51)";
(52) 1-(5-isoquinolinesulfonyl)-2-phenylpiperazine referred to as "Compound (52)";
(53) 1-(5-isoquinolinesulfonyl)-3-phenylpiperazine referred to as "Compound (53)";
(54) 1-(5-isoquinolinesulfonyl)-3-benzylpiperazine referred to as "Compound (54)";
(55) 1-(5-isoquinolinesulfonyl)-4-phenylpiperazine referred to as "Compound (55)";
(56) 1-(5-isoquinolinesulfonyl)-4-benzylpiperazine referred to as "Compound (56)";
(57) 1-(5-isoquinolinesulfonyl)-4-phenethylpiperazine referred to as "Compound (57)";
(58) 1-(5-isoquinolinesulfonyl)-4-benzoylpiperazine referred to as "Compound (58)";
(59) 1-(5-isoquinolinesulfonyl)-4-cinnamylpiperazine referred to as "Compound (59)";
(60) 1-(5-isoquinolinesulfonyl)-4-cinnamoylpiperazine referred to as "Compound (60)";
(61) 1-(5-isoquinolinesulfonyl)-4-furoylpiperazine referred to as "Compound (61)";
(62) 1-(5-isoquinolinesulfonyl)-4-(2-methoxy-2-phenylethyl)piperazine referred to as "Compound (62)";
(63) 1-(5-isoquinolinesulfonyl)-4-(2-ethoxy-2-phenylethyl)piperazine referred to as "Compound (63)";
(64) 1-(5-isoquinolinesulfonyl)-4-(2-isobutoxy-2-phenylethyl)piperazine referred to as "Compound (64)";
(65) N-[2-(N-methyl-N-benzylamino)ethyl]-5-isoquinolinesulfonamide referred to as "Compound (65)";
(66) N-[2-(N-ethyl-N-benzylamino)ethyl]-5-isoquinolinesulfonamide referred to as "Compound (66)";
(67) N-[2-(N-isopropyl-N-benzylamino)ethyl]-5-isoquinolinesulfonamide referred to as "Compound (67)";
(68) 1-(5-isoquinolinesulfonyl)-3,3-dimethylpiperazine referred to as "Compound (68)";
and the pharmaceutically acceptable acid addition salts thereof.

The acid addition salts of the isoquinolinesulfonyl derivatives of Formula (I) according to this invention are pharmaceutically acceptable non-toxic salts and can be prepared by conventional methods.

Suitable examples of such pharmaceutically acceptable acid addition salts include the salts of inorganic acids such as hydrochloric acid, hydrobromic acid, phosphoric acid, and sulfuric acid; and the salts of organic acids such as acetic acid, citric acid, tartaric acid, lactic acid, succinic acid, fumaric acid, maleic acid, methanesulfonic acid and p-toluenesulfonic acid.

The isoquinolinesulfonyl derivatives of Formula (I) of this invention can be prepared by reacting a 5-isoquinolinesulfonyl chloride of Formula (II) with a compound of Formula (III) in accordance with the following equation:

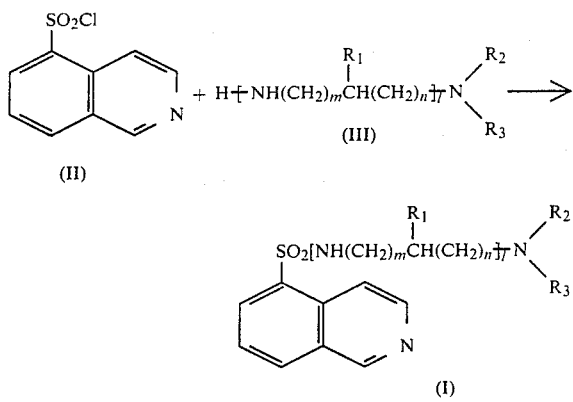

wherein l, m, n, $R_1$, $R_2$ and $R_3$ are the same as defined above.

Exemplary compounds of Formula (III) include 1,2-diaminoethane, 1,3-diaminopropane, 1,4-diaminobutane, 1,5-diaminopentane, 1,6-diaminohexane, 1,8-diaminooctane, 1,10-diaminodecane, methylamine, ethylamine, n-propylamine, isopropylamine, n-butylamine, isobutylamine, n-hexylamine, dimethylamine, diethylamine, di-n-2-(N-methyl-N-benzylamino)ethylamine, 2-(N-ethyl-N-benzylamino)ethylamine, 2-(N-isopropyl-N-benzylamino)ethylamine, butylamine, di-n-hexylamine, 3-(N,N-dimethylamino)propylamine, 3-(N,N-diethylamino)propylamine, 3-(di-n-propylamino)propylamine, 3-diisopropylamino)propylamine, 3-(di-n-butylamino)propylamine, 3-(diisobutylamino)propylamine, 3-(N-methyl-N-cyclohexylamino)propylamine, 3-(N-methyl-N-phenylamino)propylamine, 3-(N-methyl-N-benzylamino)propylamine, 3-piperidinopropylamine, 3-pyrrolidinopropylamine, 3-morpholinopropylamine, piperidine, piperazine, morpholine, pyrrolidine, 2-methylpiperazine, 1-methylpiperazine, 2-ethylpiperazine, 1-ethylpiperazine, 2-n-propylpiperazine, 1-n-propylpiperazine, 2-isopropylpiperazine, 1-isopropylpiperazine, 2-n-butylpiperazine, 1-n-butylpiperazine, 2-isobutylpiperazine, 1-isobutylpiperazine, 2-n-hexylpiperazine, 1-n-hexylpiperazine, 2,2-dimethylpiperazine, 2,3-dimethylpiperazine, 2,5-dimethylpiperazine, 2,6-dimethylpiperazine, 2,5-diethylpiperazine, 2-isobutyl-5-methylpiperazine, 2-benzyl-5-methylpiperazine, 2-phenylpiperazine, 1-phenylpiperazine, 2-benzylpiperazine, 1-benzylpiperazine, 1-phenethylpiperazine, 1-benzoylpiperazine, 1-cinnamylpiperazine, 1-cinnamoylpiperazine, 1-furoylpiperazine, 1-(2-methoxy-2-phenylethyl)piperazine, 1-(2-ethoxy-2-phenylethyl)piperazine and 1-(2-isobutoxy-2-phenylethyl)piperazine.

The reaction between the compound of Formula (II) and the compound of Formula (III) can be carried out in the presence of absence of an acid acceptor. Exemplary acid acceptor which can be employed include alkali metal compounds such as a hydroxide, bicarbonate, carbonate, hydride or an alkoxide, e.g. sodium bicarbonate, sodium carbonate, potassium carbonate, sodium hydroxide, potassium hydroxide, sodium hydride and sodium alkoxides such as sodium methoxide, sodium ethoxide and sodium tert-butoxide; and organic tertiary amines such as trimethylamine, triethylamine, 1,4-diazabicyclo[2,2,2]octane and pyridine.

In general, this reaction is carried out in the presence of a reaction medium. Exemplary reaction media which can be employed include halogenated hydrocarbons such as chloroform and dichloromethane; alcohols such as methanol, ethanol and butanol; ethers such as tetrahydrofuran and dioxane; N,N-dimethylformamide, dimethyl sulfoxide, acetonitrile and water. The reaction media may be used singly or in combination with one another.

The amount of the compound of Formula (III) which can be employed is at least 1 mol and typically ranges from 1 to about 20 mols, preferably from 1 to 10 mols per mol of the compound of Formula (II). A more preferred amount of the compound of Formula (III) ranges from 1 to 5 mols per mol of the compound of Formula (II) when the acid acceptor is present, and from 2 to 10 mols per mol of the compound of Formula (II) when the acid acceptor is absent. This amount, however, does not apply to amines having a low boiling point such as methylamine and ethylamine.

The amount of the acid acceptor employed is preferably about 0.5 to about 10 equivalents and more preferably about 1 to about 6 equivalents for each mol of the compound of Formula (III).

The reaction between the compound of Formula (II) and the compound of Formula (III) can be carried out typically at a temperature of from about $-30°$ C. to about $150°$ C. and preferably from about $0°$ C. to about $30°$ C.

While this reaction can be carried out at a pressure above atmospheric, it is generally advisable to utilize atmospheric pressure.

The reaction time which can be employed is typically about 0.5 to about 48 hours and preferably about 0.5 to 20 hours at atmospheric pressure.

Also, when $R_2$ in Formula (I) is a hydrogen atom, the 5-isoquinolinesulfonyl derivatives of this invention represented by Formula (VI) can be prepared by the following equations:

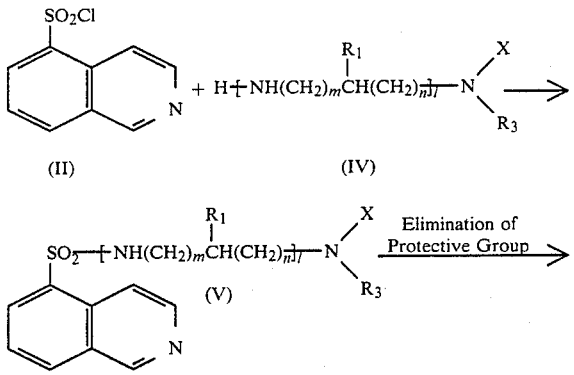

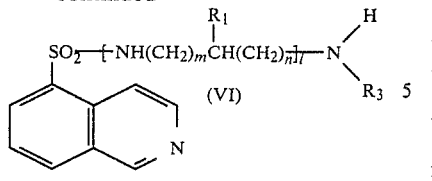

(VI)

Further, when l in Formula (I) is zero, the

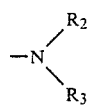

group in Formula (I) is a

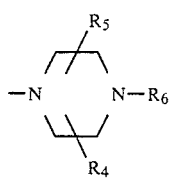

group and $R_6$ is a hydrogen atom, the 5-isoquinolinesulfonyl derivatives of this invention represented by Formula (IX) can be prepared in accordance with the following equations:

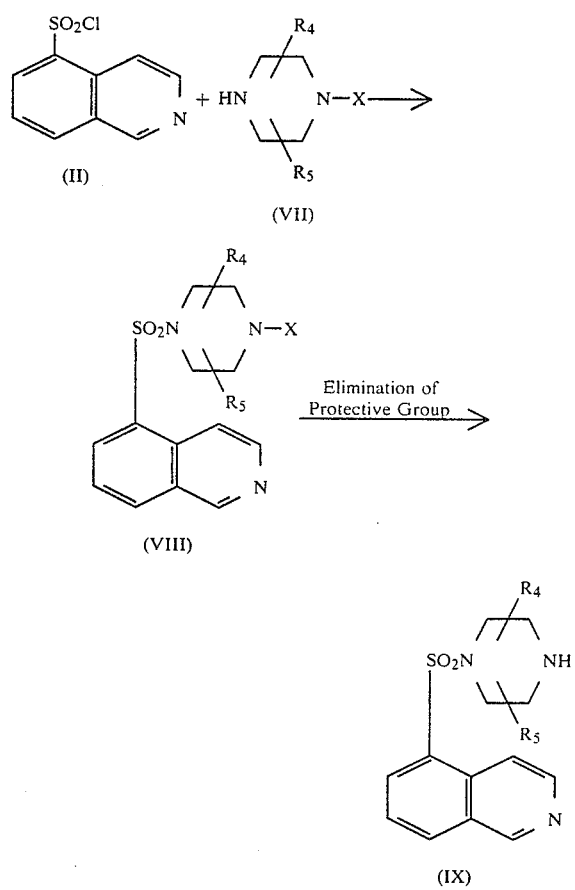

In these Formulae, l, m, n, $R_1$, $R_3$, $R_4$ and $R_5$ are the same as defined above and X is a protective group. Exemplary protective groups represented by X which can be employed in this invention include acyl groups such as formyl, acetyl and benzoyl; arylmethyloxycarbonyl groups such as benzyloxycarbonyl; alkyloxycarbonyl groups such as tert-butoxycarbonyl; and benzyl group.

Exemplary compounds of Formulae (IV) and (VII) include $N^1$-acetyl-1,2-diaminoethane, $N^1$-acetyl-1,3-diaminopropane, $N^1$-acetyl-1,4-diaminobutane, $N^1$-acetyl-1,5-diaminopentane, $N^1$-acetyl-1,6-diaminohexane, $N^1$-acetyl-1,8-diaminooctane, $N^1$-acetyl-1,10-diaminodecane, 2-benzyloxycarbonylamino-1-methylethylamine, 1-(benzyloxycarbonylaminomethyl)propylamine, 1-(benzyloxycarbonylaminomethyl)pentylamine, 2-(benzyloxycarbonylamino)propylamine, 2-(benzyloxycarbonylamino)-3-methylbutylamine, 2-acetamidopropylamine, 2acetamido-3-methylbutylamine, 2-acetamido-2-phenylethylamine, 2-(N-benzyl-N-methylamino)ethylamine, 2-(N-benzyl-N-ethylamino)ethylamine, 2-(N-benzyl-N-isopropylamino)ethylamine, 2-(benzyloxycarbonylamino)-1-phenylethylamine, 2-(benzyloxycarbonylamino)-2-phenylethylamine, 1-formyl-3-methylpiperazine, 1-acetyl-3-methylpiperazine, 1-benzyloxycarbonyl-3-methylpiperazine, 1-t-butyloxycarbonyl-3-methylpiperazine, 1-benzyl-3-methylpiperazine, 1-benzyloxycarbonyl-3-ethylpiperazine and 1-benzyloxycarbonyl-3-phenylpiperazine.

The reaction between the compound of Formula (II) and the compound of Formula (IV) and the reaction between the compound of Formula (II) and the compound of Formula (VII) can be carried out under the same reaction conditions as in the reaction between the compound of Formula (II) and the compound of Formula (III) to give the compound of Formula (V) and the compound of Formula (VIII), respectively. The method of obtaining the desired compound of Formula (VI) and the desired compound of Formula (IX) from the compound of Formula (V) and the compound of Formula (VIII), respectively, may vary depending upon the protective group of X selected, generally known methods can be employed in this invention. For example, when the protective group of X is an acyl group such as formyl or acetyl, the desired compounds can be obtained by hydrolysis with an acid or an alkali. When the protective group of X is a benzyl group, the desired compounds can be obtained by hydrogenation. When the protective group of X is an arylmethyloxycarbonyl group such as benzyloxycarbonyl, the desired compounds can be obtained by hydrogenation or hydrolysis with an acid. When the protective group of X is an alkyloxycarbonyl group such as tert-butoxycarbonyl, the desired products can be obtained by hydrolysis with an acid.

Furthermore, when l in Formula (I) is zero, the

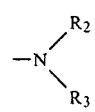

group in Formula (I) is a

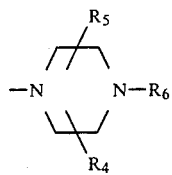

group and $R_6$ is not a hydrogen atom, the 5-isoquinolinesulfonyl derivatives of this invention represented by Formula (XII) can be prepared in accordance with the following equations:

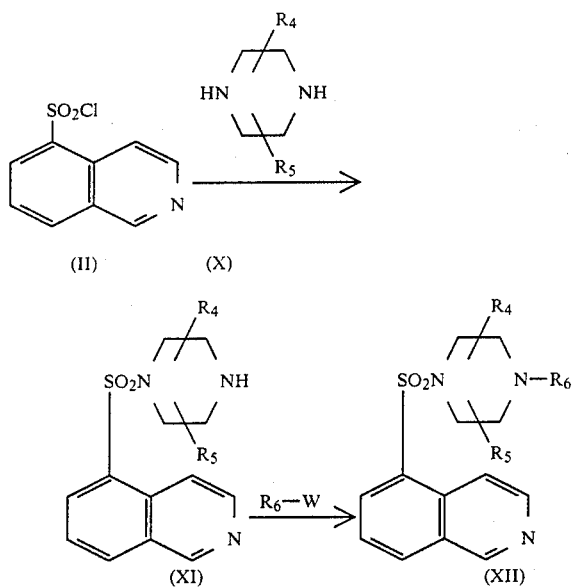

In these Formulae, $R_4$, $R_5$ and $R_6$ are the same as defined above and W is an elimination group. Exemplary elimination groups include halogen atoms such as chlorine, bromine and iodine; substituted sulfonyloxy groups such as p-toluenesulfonyloxy and methanesulfonyloxy; and sulfuric acid residue. Exemplary compounds of the formula, $R_6$-W which can be employed include dimethyl sulfate, methyl iodide, diethyl sulfate, ethyl bromide, n-propyl iodide, n-propyl bromide, isopropyl bromide, n-butyl bromide, isobutyl bromide, n-hexyl bromide, n-hexyl-p-toluenesulfonate, benzyl chloride, benzyl bromide, phenethyl bromide, benzoyl chloride, cinnamyl chloride, cinnamoyl chloride, furoyl chloride, 2-methoxy-2-phenylethyl bromide, 2-ethoxy-2-phenylethyl bromide and 2-isobutoxy-2-phenylethyl bromide.

In general, the reaction between the compound of Formula (XI) and the compound of $R_6$-W can be carried out in the presence of an acid acceptor. Exemplary acid acceptors which can be employed include the same ones as employed in the reaction between the compound of Formula (II) and the compound of Formula (III).

This reaction is, in general, carried out in the presence of a reaction medium. Exemplary reaction media which can be employed include the same one as employed in the reaction between the compound of Formula (II) and the compounds of Formula (III).

The amount of the compound of $R_6$-W which can be employed is at least 1 mol and typically ranges from 1 mol to about 20 mols, preferably from 1.2 mol to 10 mols per mol of the compound of Formula (XI).

The amount of the acid acceptor employed is preferably about 1 to about 10 equivalents and more preferably 1 to 4 equivalents for each mol of the compound of Formula (III).

The reaction between the compound of Formula (XI) and the compound of $R_6$-W can be carried out typically at a temperature of from about $-30°$ C. to about $200°$ C. and preferably from about $0°$ C. to about $100°$ C.

While this reaction may be carried out at a pressure above atmospheric or under reduced pressure, it is advisable to employ atmospheric pressure for practical purposes.

The method of separating and purifying the isoquinolinesulfonyl derivative of Formula (I) from the reaction solution comprises extracting the compound of Formula (I) with diluted hydrochloric acid, rendering the aqueous hydrochloric acid layer extracted basic, extracting the extract with a solvent such as chloroform capable of easily dissolving the extract, condensing the extract and subjecting the condensed residues to a silica gel column or an aluminum column chromatography for purification.

It has now been found that the isoquinolinesulfonyl derivatives of Formula (I) and the pharmaceutically acceptable salts have pharmacologically and biochemically interesting properties such as a relaxatory action for vascular smooth muscle and an action for increasing blood flow and are useful as a vasodilator, a hypotensor, an ameliorant of cerebral circulation, a medicine for angina pectoris and a preventive and a medicine for cardiovascular thrombosis.

The effect of the isoquinolinesulfonyl derivatives and the pharmaceutically acceptable acid addition salts of this invention on smooth muscle can be proved by suspending a mesenteric artery taken out from a rabbit in helical form, contracting the mesenteric artery with potassium chloride and adding the isoquinolinesulfonyl derivatives or their pharmaceutically acceptable acid addition salts of this invention to the contracted mesenteric artery, resulting in the relaxation of the mesenteric artery. When, for example, 1-(5-isoquinolinesulfonyl)-4-methylpiperazine, i.e., Compound (36) was added and a complete relaxation was designated 100%, the concentration which could bring about a relaxation of 50%, i.e., $ED_{50}$ was 7.7 $\mu$M, and with 1-(5-isoquinolinesulfonyl)piperazine, i.e., Compound (35) and N-(4-aminobutyl)-5-isoquinoline sulfonamide, i.e., Compound (3), $ED_{50}$ were 0.6 $\mu$M and 11 $\mu$M, respectively.

The effect of the isoquinolinesulfonyl derivatives and the pharmaceutically acceptable acid addition salts of this invention on the vasodilatation of the femoral and vertebral arteries can be measured by anesthetizing a dog of mixed breed weighting 8 to 15 Kg by an intravenous administration of 35 mg/Kg of pentbarbital, providing an acute type probe (a product of Nippon Koden K.K., Japan) with the femoral and vertebral arteries, administering the isoquinolinesulfonyl derivatives and the pharmaceutically acceptable acid addition salts to the femoral vein through a polyethylene tube inserted into the femoral vein side chain and measuring the blood flow volume with an electromagnetic flowmeter (a product of Nippon Koden K.K., Japan, "MF-27"). Among the isoquinolinesulfonyl compounds of Formula (I) of this invention, those with l=0 and the

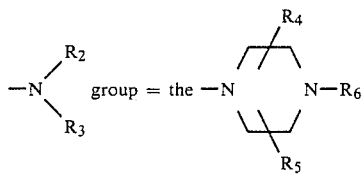

group show a high action for increasing blood flow and simultaneously a selectivity to vertebral arteries. For example, when 1 mg/Kg of 1-(5-isoquinolinesulfonyl)-piperazine, i.e., Compound (35) was intravenously administered, the increased blood flow volumes in the vertebral artery and in the femoral artery were 98% and 65%, respectively. Also the isoquinolinesulfonyl compounds of Formula (I) of this invention with $l=1$ and one of the $R_2$ and $R_3$ groups=a hydrogen atom show a continuing blood flow increase. With 1 mg/Kg of N-(2-aminoethyl)-5-isoquinolinesulfonamide, i.e., Compound (1), an increase in the blood flow volume in the vertebral artery was continued for at least 30 minutes.

Furthermore, when the isoquinolinesulfonyl derivatives and the pharmaceutically acceptable acid addition salts of this invention are intravenously and arterially administered for the above described purposes, any remarkable toxicity cannot be observed. For example, the acute toxicity of 1-(5-isoquinolinesulfonyl)-4-methylpiperazine, i.e., Compound (36), i.e., $LD_{50}$ was 94 mg/Kg in giving male ddY-strain mice an intravenous administration.

The following examples illustrate the present invention in more detail, but they are given for illustrative purposes only and are not to be construed as limiting the invention.

The following examples illustrate the present invention in more detail, but they are given for illustrative purposes only and are not to be construed as limiting the invention.

EXAMPLE 1

In 200 ml of chloroform was dissolved 8.8 g of 1,4-diaminobutane, and to the solution was added dropwise 100 ml of a chloroform solution containing 4.55 g of 5-isoquinolinesulfonyl chloride under cooling with ice. After the dropwise addition of the chloroform solution, the mixed solution was stirred at a temperature of 20° C. to 25° C. for two hours, and then the reaction solution was extracted with a 10% aqueous hydrochloric acid solution. The pH of the aqueous layer was adjusted to 10 with a 10% aqueous sodium hydroxide solution, and the aqueous layer was extracted with chloroform. The chloroform layer extracted was washed with water and dried with anhydrous potassium carbonate. Then the chloroform was distilled from the chloroform layer, and the residue obtained was subjected to a column chromatography [silica gel: 200 g; developing solvent: 2% methanol/chloroform (volume ratio)] to give 3.46 g of N-(4-aminobutyl)-5-isoquinolinesulfonamide, i.e., Compound (3) as an oily substance in a yield of 62%.

Mass spectrum (m/e): 279(M+) and 221.

NMR spectrum (CDCl$_3$): 1.5~2.0(4H, 2×C$\underline{H}_2$), 2.5~3.2(4H, 2×NC$\underline{H}_2$), 2.4(2H, N$\underline{H}_2$), 7.5~7.7(1H), 7.9~8.7(4H) and 9.3(1H).

IR absorption spectrum ($\nu_{max}^{cap}$, cm$^{-1}$): 1330 and 1160.

The same procedures as described above were repeated using the compounds of Formula (III) as set forth in Table 1-1 under the reaction conditions as set forth in Table 1-1, and N-(ω-aminoalkyl)-5-isoquinoline sulfonamides as set forth in Table 1-2 were obtained. The results and the analytical values of these compounds are shown in Table 1-2.

TABLE 1-1

| Run No. | SO$_2$Cl-isoquinoline (g) | Compound of Formula (III) (g) | Reaction Temperature (°C.) | Reaction Time (hour) |
|---|---|---|---|---|
| 1 | 4.55 | H$_2$N(CH$_2$)$_2$NH$_2$  12.0 | 15~20 | 2 |
| 2 | 3.41 | H$_2$N(CH$_2$)$_3$NH$_2$  11.1 | " | 2 |
| 3 | 4.55 | H$_2$N(CH$_2$)$_6$NH$_2$  11.6 | " | 5 |
| 4 | 2.28 | H$_2$N(CH$_2$)$_{10}$NH$_2$  8.62 | " | 10 |

TABLE 1-2

SO$_2$NH(CH$_2$)$_n$NH$_2$ isoquinoline

| Run No. | Compound No. | n | Yield [g] | (%) | Mass Spectrum (m/e) | IR Absorption Spectrum ($\nu$SO$_2$, cm$^{-1}$) | NMR Spectrum (CDCl$_3$) |
|---|---|---|---|---|---|---|---|
| 1 | (1) | 2 | 3.3 | (66) | 222, 221 193, 129 128 | 3400, 1610 1330, 1165 1145, 1190 1030, 830 | 1.5(2H, N$\underline{H}_2$), 2.9(4H, 2 × C$\underline{H}_2$) 7.58~7.9(1H), 8.0~8.7(4H) 9.33(1H) |
| 2 | (2) | 3 | 2.9 | (73) | 265, 236 221, 143 128 | 3400, 1610 1350, 1330 1160, 1145 1090, 830 | 1.4~1.9(2H, C$\underline{H}_2$) 2.5~3.2(4H, 2 × NC$\underline{H}_2$) 3.21(2H, N$\underline{H}_2$), 7.62(1H) 8.0~8.8(4H), 9.33(1H) |
| 3 | (4) | 6 | 4.6 | (75) | 307, 277 263, 243 221, 192 128 | 1590, 1320 1140, 1120 1060, 810 | 1.0~2.0(8H), 2.9~3.2(4H) 7.65(1H), 8.0~8.8(4H) 9.33(1H) |

TABLE 1-2-continued

SO₂NH(CH₂)ₙNH₂ — (isoquinoline structure)

| Run No. | Compound No. | n | Yield [g] | Yield (%) | Mass Spectrum (m/e) | IR Absorption Spectrum ($\nu SO_2$, cm$^{-1}$) | NMR Spectrum (CDCl₃) |
|---|---|---|---|---|---|---|---|
| 4 | (5) | 10 | 2.2 | (61) | 363, 320 292, 221 192, 128 | 3400, 1590 1350, 1330 1160, 1140 | 1.3(16H, 8 × C$\underline{H}_2$) 2.5~3.2(4H, 2 × NC$\underline{H}_2$) 3.3(2H, N$\underline{H}_2$), 7.0(1H, N$\underline{H}$) 7.6(1H), 8.1~8.8(4H) 9.3(1H) |

EXAMPLE 2

In 50 ml of dichloromethane was dissolved 1.73 g of 5-isoquinolinesulfonyl chloride, and to the solution were added 1.54 g of triethylamine and 8.0 g of monomethylamine hydrochloride. The mixture was stirred at a temperature of 10° C. to 15° C. for 18 hours. The reaction solution obtained was washed with water, dried with magnesium sulfate, and then the dichloromethane was distilled therefrom under reduced pressure. The residue obtained was subjected to a silica gel column chromatography (silica: 50 g; solvent: chloroform) to give 1.30 g of N-methyl-5-isoquinolinesulfonamide, i.e., Compound (25) in a yield of 77%.

Mass spectrum (m/e): 208, 148 and 128.

NMR spectrum (CDCl₃): 2.63(3H, singlet, NC$\underline{H}_3$), 3.23(1H, N$\underline{H}$), 7.4~7.7(1H), 8.1~8.7(4H) and 9.3(1H).

IR absorption spectrum ($\nu_{max}^{cap}$, cm$^{-1}$): 3050, 2920, 1610, 1580, 1440, 1365, 1320, 1210, 1150, 1130 and 1080.

The same procedures as described above were repeated using the compounds of Formula (III) as set forth in Table 2-1 under the reaction conditions as set forth in Table 2-1, and there were obtained N-ethyl-5-isoquinolinesulfonamide, i.e., Compound (26); N,N-dimethyl-5-isoquinolinesulfonamide, i.e., Compound (29); and N,N-diethyl-5-isoquinolinesulfonamide, i.e., Compound (30). The results and the analytical values of these compounds are shown in Table 2-2.

TABLE 2-1

SO₂Cl — (isoquinoline structure)

| Run No. | (g) | Compound of Formula (III) | (g) | N(C₂H₅)₃ (g) | Reaction Temperature (°C.) | Reaction Time (hour) |
|---|---|---|---|---|---|---|
| 1 | 2.28 | H₂N(C₂H₅).HCl | 8.2 | 10 | 15~25 | 24 |
| 2 | " | HN(CH₃)₂.HCl | 8.2 | 10 | " | 20 |
| 3 | 1.50 | HN(C₂H₅)₂.HCl | 7.2 | 6.6 | " | " |

TABLE 2-2

SO₂Y — (isoquinoline structure)

| Run No. | Compound No. | Y | Yield [g] | Yield (%) | Mass Spectrum (m/e) | IR Absorption Spectrum ($\nu_{max}^{cap}$, cm$^{-1}$) | NMR Spectrum (CDCl₃) |
|---|---|---|---|---|---|---|---|
| 1 | (26) | —NH(C₂H₅) | 1.93 | (81) | 236, 164 128 | 3050, 2920 1600, 1560 1440, 1360 1300, 1200 1150, 1070 | 1.15(3H, triplet) 2.73(2H, quartet) 3.33(1H, singlet, N$\underline{H}$) 7.4~7.7(1H) 8.1~8.7(4H), 9.32(1H) |
| 2 | (29) | —N(CH₃)₂ | 1.77 | (75) | 236, 191 143, 128 | 1600, 1470 1440, 1320 1145, 1125 1035, 975 940 | 2.85(6H, 2 × C$\underline{H}_3$) 7.5~7.9(1H) 8.2~8.5(4H), 9.3(1H) |
| 3 | (30) | —N(C₂H₅)₂ | 1.34 | (77) | 264, 235 191, 143 | 1600, 1460 1360, 1150 1120, 1050 | 1.2~1.4(6H, 2 × C$\underline{H}_3$) 2.2~3.3(4H, 2 × NC$\underline{H}_2$) 7.5~8.6(5H), 9.3(1$\underline{H}$) |

EXAMPLE 3

In 100 ml of methylene chloride were added 6.0 g of piperazine and 1.2 g of anhydrous potassium carbonate, and to the mixture was added dropwise 30 ml of a methylene chloride solution containing 2.0 g of 5-isoquinolinesulfonyl chloride under cooling with ice. After the dropwise addition of the methylene chloride solution, the mixed solution was stirred at a temperature of 15° C. to 25° C. for 15 hours, and then the reaction solution was washed with water, dried with anhydrous magnesium sulfate, and the methylene chloride was distilled therefrom. The residue thus obtained was subjected to a silica gel column chromatography (silica gel:

70 g; solvent: chloroform) to give 2.14 g of 1-(5-isoquinolinesulfonyl)piperazine, i.e., Compound (35) in a yield of 89%.

Mass spectrum (m/e): 277, 234, 212, 191 and 128.

NMR spectrum (CDCl$_3$): 1.65(1H, N$\underline{H}$), 2.8~3.3(8H, 4×NC$\underline{H}_2$), 7.5~7.9(1H), 8.2~8.7(4H) and 9.35(1H).

IR absorption spectrum ($\nu_{max}^{KBr}$, cm$^{-1}$): 3350, 1600, 1560, 1540, 1370 and 1160.

EXAMPLE 4

In 100 ml of dichloromethane was dissolved 2.28 g of 5-isoquinolinesulfonyl chloride, and to the solution were added 1.38 g of anhydrous potassium carbonate and 1.46 g of n-butylamine, and the mixture thus obtained was stirred at a temperature of 20° C. to 25° C. for 12 hours. The reaction solution was washed with water, dried with anhydrous magnesium sulfate, and the dichloromethane was distilled therefrom under reduced pressure. The residue thus obtained was subjected to a silica gel column chromatography (silica gel: 70 g; solvent: chloroform) to give 1.90 g of N-n-butyl-5-isoquinolinesulfonamide, i.e., Compound (27) in a yield of 72%.

Mass spectrum (m/e): 264, 211 and 191.

NMR spectrum (CDCl$_3$): 0.7~1.6(7H, C$_3$$\underline{H}_7$), 2.67(2H, NC$\underline{H}_2$), 3.46(1H, N$\underline{H}$), 7.4~7.8(1H), 8.1~8.6(4H) and 9.3(1H).

IR absorption spectrum ($\nu_{max}^{cap}$, cm$^{-1}$): 3070, 2920, 1610, 1580, 1450, 1360, 1300, 1150, 1080.

The same procedures as described above were repeated using the compounds of Formula (III) as set forth in Table 3-1 under the reaction conditions as set forth in Table 3-1, and there were obtained N-isobutyl-5-isoquinolinesulfonamide, i.e., Compound (28); N,N-di-n-butyl-5-isoquinolinesulfonamide, i.e., Compound (31); 1-(5-isoquinolinesulfonyl)piperazine, i.e., Compound (32); 1-(5-isoquinolinesulfonyl)pyrrolidine, i.e., Compound (33); and 1-(5-isoquinolinesulfonyl)morpholine, i.e., Compound (34). The results and the analytical values of these compounds are shown in Table 3-2.

TABLE 3-1

| Run No. | (g) | Compound of Formula (III) | (g) | Anhydrous Potassium Carbonate (g) | Reaction Temperature (°C.) | Reaction Time (hour) |
|---|---|---|---|---|---|---|
| 1 | 3.0 | H$_2$N(i-C$_4$H$_9$) | 2.4 | 2.1 | 20~25 | 5 |
| 2 | 2.5 | HN(n-C$_4$H$_9$)$_2$ | 3.6 | 1.6 | " | 18 |
| 3 | 3.0 | HN⟨piperidine⟩ | 2.8 | 2.1 | " | 12 |
| 4 | " | HN⟨pyrrolidine⟩ | 2.5 | " | " | " |
| 5 | " | HN⟨morpholine⟩ | 2.8 | " | " | " |

TABLE 3-2

| Run No. | Compound No. | Y | Yield [g] | (%) | Mass Spectrum (m/e) | IR Absorption Spectrum ($\nu_{max}^{cap}$, cm$^{-1}$) | NMR Spectrum (CDCl$_3$) |
|---|---|---|---|---|---|---|---|
| 1 | (28) | —NH(i-C$_4$H$_9$) | 2.37 | (68) | 264, 211, 191 | 3070, 2920, 1610, 1580, 1440, 1365, 1320, 1210, 1150, 1090 | 0.7~1.1(6H, 2 × C$\underline{H}_3$), 1.0~1.5(1H, C$\underline{H}$), 2.55(2H, NC$\underline{H}_2$), 3.62(1H, N$\underline{H}$), 7.5~7.8(1H), 8.1~8.6(4H), 9.3(1H) |
| 2 | (31) | —N(n-C$_4$H$_9$)$_2$ | 2.43 | (69) | 320, 234, 191, 143 | 1600, 1470, 1360, 1150 | 0.9~1.9(14H, 2 × C$\underline{H}_2$CH$_2$CH$_3$), 2.9~3.5(4H, 2 × NC$\underline{H}_2$), 7.5~8.8(5H), 9.3(1H) |
| 3 | (32) | —N⟨piperidine⟩ | 2.6 | (71) | 276, 211, 191, 127 | 1600, 1560, 1470, 1370, 1150 | 1.4~1.9(6H, 3 × C$\underline{H}_2$), 3.0~3.3(4H, 2 × NC$\underline{H}_2$), 7.6~7.9(1H), 8.2~8.8(4H), 9.4(1H) |

TABLE 3-2-continued

| Run No. | Compound No. | Y | Yield [g] | (%) | Mass Spectrum (m/e) | IR Absorption Spectrum ($\nu_{max}^{cap}$, cm$^{-1}$) | NMR Spectrum (CDCl$_3$) |
|---|---|---|---|---|---|---|---|
| 4 | (33) | —N⟨pyrrolidine⟩ | 2.94 | (85) | 262, 211, 191, 127 | 1600, 1550, 1470, 1350, 1150 | 1.3~1.9(4H, 2 × C$\underline{H}_2$) 3.0~3.5(4H, 2 × NC$\underline{H}_2$) 7.6~7.9(1H) 8.2~8.8(4H), 9.3(1H) |
| 5 | (34) | —N⟨morpholine⟩O | 2.9 | (79) | 278, 234, 213, 191, 127 | 1590, 1560, 1540, 1470, 1370, 1150 | 3.0~3.3(4H, 2 × NC$\underline{H}_2$) 3.6~3.8(4H, 2 × OC$\underline{H}_2$) 7.5~7.9(1H) 8.0~8.7(4H), 9.3(1H) |

EXAMPLE 5

In 50 ml of a chloroform solution containing 1.4 g of 3-dimethylaminopropylamine and 1.4 g of triethylamine was added dropwise 30 ml of a chloroform solution containing 2.6 g of 5-isoquinolinesulfonyl chloride under cooling with ice. After the dropwise addition of the chloroform solution, the mixed solution was stirred at a temperature of 2° C. to 10° C. for four hours, and the reaction mixture solution was washed with water and dried with anhydrous magnesium sulfate. After the chloroform was distilled therefrom, the residue obtained was subjected to a silica gel column chromatography (silica gel: 70 g; solvent: chloroform) to give 2.38 g of N-(3-dimethylaminopropyl)-5-isoquinolinesulfonamide, i.e., Compound (17) in a yield of 71%.

Mass spectrum (m/e): 293, 249, 235, 221 and 207.

NMR spectrum (CDCl$_3$): 1.6(2H, C$\underline{H}_2$), 2.0~2.6(8H, 2×NCH$_3$+NC$\underline{H}_2$), 3.1(2H, NC$\underline{H}_2$), 6.2(N$\underline{H}$), 7.4~7.7(1H), 8.0~8.6(4H) and 9.3(1$\underline{H}$).

IR absorption spectrum ($\nu_{max}^{cap}$, cm$^{-1}$): 2950, 2860, 2840, 1460, 1320, 1150, 1130, 830 and 760.

The same procedures as described above were repeated using the compounds of Formula (III) as set forth in Table 4-1 under the reaction conditions as set forth in Table 4-1, and there were obtained N-(3-diethylaminopropyl)-5-isoquinolinesulfonamide, i.e., Compound (18); N-(3-di-n-butylaminopropyl)-5-isoquinolinesulfonamide, i.e., Compound (19); N-(3-piperidinopropyl)-5-isoquinolinesulfonamide, i.e., Compound (20); N-(3-morpholinopropyl)-5-isoquinolinesulfonamide, i.e., Compound (21); N-[3-(N-methyl-N-cyclohexylamino)propyl]-5-isoquinolinesulfonamide, i.e., Compound (22); N-[3-(N-methyl-N-phenylamine)propyl]-5-isoquinolinesulfonamide, i.e., Compound (23); and N-[3-(N-methyl-N-benzylamino)propyl]-5-isoquinolinesulfonamide, i.e., Compound (24). The results and the analytical values of these compounds are shown in Table 4-2.

TABLE 4-1

| Run No. | SO$_2$Cl-isoquinoline (g) | H$_2$N(CH$_2$)$_3$N(R$_2$)(R$_3$) (g) | N(C$_2$H$_5$)$_3$ (g) | Reaction Temperature (°C.) | Reaction Time (hour) |
|---|---|---|---|---|---|
| 1 | 1.0 | H$_2$N(CH$_2$)$_3$N(C$_2$H$_5$)$_2$ | 0.7 | 0.67 | 2~5 | 5 |
| 2 | " | H$_2$N(CH$_2$)$_3$N(n-C$_4$H$_9$)$_2$ | 1.0 | " | 5~10 | " |
| 3 | " | H$_2$N(CH$_2$)$_3$N⟨piperidine⟩ | 0.8 | " | 10~20 | 12 |
| 4 | " | H$_2$N(CH$_2$)$_3$N⟨morpholine⟩O | 0.8 | " | 15~25 | 18 |
| 5 | 0.44 | H$_2$N(CH$_2$)$_3$N(CH$_3$)(cyclohexyl) | 0.4 | 0.3 | " | " |

TABLE 4-1-continued

Structure: 5-SO₂Cl-isoquinoline + H₂N(CH₂)₃N(R₂)(R₃)

| Run No. | (g) | (g) | N(C₂H₅)₃ (g) | Reaction Temperature (°C.) | Reaction Time (hour) |
|---|---|---|---|---|---|
| 6 | " | H₂N(CH₂)₃N(CH₃)(C₆H₅) | 0.38 | " | " |
| 7 | 0.75 | H₂N(CH₂)₃N(CH₃)(CH₂C₆H₅) | 0.75 | 0.5 | " | " |

TABLE 4-2

Structure: 5-SO₂NH(CH₂)₃N(R₂)(R₃)-isoquinoline

| Run No. | Compound No. | —N(R₂)(R₃) | Yield [g (%)] | Mass Spectrum (m/e) | IR Absorption Spectrum ($\nu_{max}^{cap}$, cm⁻¹) | NMR Spectrum (CDCl₃) |
|---|---|---|---|---|---|---|
| 1 | (18) | —N(C₂H₅)₂ | 0.75 (53) | 321, 249; 235, 221; 207, 192 | 2950, 2850; 1460, 1320; 1160, 1130 | 1.1(6H, 2 × CH₃); 1.5~2.0(2H, CH₂); 2.0~2.6(6H, 3 × NCH₂); 3.1(2H, NCH₂), 6.8(1H, NH); 7.6(1H, 8.0~8.5(4H); 9.3(1H) |
| 2 | (19) | —N(n-C₄H₉)₂ | 0.93 (56) | 377, 334; 296, 248; 234, 220; 140 | 2960, 2870; 1460, 1325; 1155, 1135 | 0.8~2.0(16H, 2 × CH₃ + 5 × CH₂); 2.2~2.8(6H, 3 × NCH₂); 3.1(2H, NCH₂), 5.4(1H, NH); 7.7(1H, 8.1~8.7(4H), 9.3(1H) |
| 3 | (20) | —N(piperidine) | 0.72 (49) | 332, 248; 234, 220; 206, 191 | 3075, 2920; 2850, 2800; 1320, 1160 | 1.3~2.0(8H, 4 × CH₂); 2.0~2.6(6H, 3 × NCH₂); 3.0(2H, NCH₂), 6.8(1H, NH); 7.6(1H, 8.1~8.7(4H), 9.3(1H) |
| 4 | (21) | —N(morpholine) | 0.63 (43) | 334, 278; 276, 248; 234, 221; 192, 143; 128 | 2950, 2850; 2820, 1320; 1160, 1140; 1120, 760 | 1.3~1.9(2H, CH₂); 2.0~2.7(6H, 3 × NCH₂); 3.0(2H, NCH₂); 3.4~3.9(4H, 2 × OCH₂); 6.5~7.1(1H, NH), 7.7(1H); 8.1~8.8(4H), 9.4(1H) |

TABLE 4-2-continued

| Run No. | Compound No. | $R_2$ / $R_3$ | Yield [g (%)] | Mass Spectrum (m/e) | IR Apsorption Spectrum ($\nu_{max}^{cap}$, cm$^{-1}$) | NMR Spectrum (CDCl$_3$) |
|---|---|---|---|---|---|---|
| 5 | (22) | 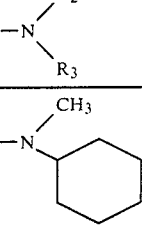 | 0.43 (62) | 361, 318 | 2930, 2850 | 0.7~1.8(12H, 6 × C$\underline{H}_2$) |
|   |   |   |   | 249, 221 | 1330, 1160 | 2.1(3H, NC$\underline{H}_3$) |
|   |   |   |   | 192, 169 | 1140, 790 | 2.1~2.8(3H, NC$\underline{H}_2$ + NC$\underline{H}$) |
|   |   |   |   | 126 | 760 | 2.7~3.1(2H, NC$\underline{H}_2$) |
|   |   |   |   |   |   | 7.1~7.5(1H, N$\underline{H}$), 7.5(1H) |
|   |   |   |   |   |   | 7.9~8.7(4H), 9.2(1H) |
| 6 | (23) | 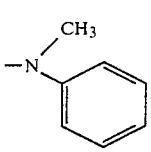 | 0.27 (39) | 355, 163 | 3050, 2900 | 1.5~1.9(2H), 2.7(3H, NC$\underline{H}_3$) |
|   |   |   |   | 134, 128 | 2850, 1620 | 2.8~3.4(4H, 2 × NC$\underline{H}_2$) |
|   |   |   |   | 120 | 1500, 1330 | 6.2(1H, N$\underline{H}$), 6.5~6.8(3H) |
|   |   |   |   |   | 1160, 1135 | 6.9~7.3(2H), 7.6(1H) |
|   |   |   |   |   | 830, 750 | 8.0~8.6(4H), 9.25(1H) |
| 7 | (24) | 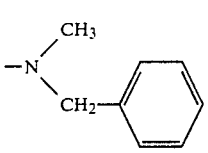 | 0.86 (71) | 369, 354 | 3050, 2950 | 1.3~1.9(2H, C$\underline{H}_2$), 1.95(3H, NC$\underline{H}_3$) |
|   |   |   |   | 278, 221 | 2850, 2800 | 2.3~2.7(2H, NC$\underline{H}_2$) |
|   |   |   |   | 177, 134 | 1620, 1450 | 3.0~3.3(2H, NC$\underline{H}_2$) |
|   |   |   |   | 128, 120 | 1330, 1210 | 3.3(2H, C$_6$H$_5$C$\underline{H}_2$) |
|   |   |   |   | 91 | 1155, 1135 | 7.0~7.1(1H, N$\underline{H}$) |
|   |   |   |   |   |   | 7.2(5H, C$_6\underline{H}_5$), 7.6(1H) |
|   |   |   |   |   |   | 8.0~8.5(4H), 9.3(1H) |

NMR spectrum (CDCl$_3$, δ): 2.9(3H, s, CH$_3$), 3.0~4.0(8H, m, 4×C$\underline{H}_2$), 7.8~8.1(1H), 8.5~8.8($\overline{4H}$) and 9.6(1H, s)

IR absorption spectrum ($\nu_{max}^{KBr}$, cm$^{-1}$): 3400, 1610, 1378, 1350, 1160 and 1140.

EXAMPLE 6

In 100 ml of chloroform was dissolved 5.0 g of 1-methylpiperazine, and to the solution was added 6.9 g of anhydrous potassium carbonate. To the mixture was added dropwise 200 ml of a chloroform solution containing 1.4 g of 5-isoquinolinesulfonyl chloride under cooling with ice. After the dropwise addition of the chloroform solution, the mixed solution thus obtained was stirred for one hour under cooling with ice, and then the reaction solution was washed with 50 ml of a 5N aqueous sodium hydroxide solution and extracted twice with 50 ml of a 5N aqueous hydrochloric acid solution. The aqueous hydrochloric acid layer was rendered alkaline, extracted three times with 100 ml of chloroform, and the chloroform layer extracted was washed with water and dried with anhydrous magnesium sulfate. After the chloroform was distilled therefrom under reduced pressure, 50 ml of a 5N aqueous hydrochloric acid solution was added to the residue and the mixture was condensed to dryness under reduced pressure. The crystalline residue thus obtained was recrystallized from ethanol to give 14.9 g of 1-(5-isoquinolinesulfonyl)-4-methylpiperazine [i.e., Compound (36)] dihydrochloride in a yield of 82%.

Melting point: 215° C.

Mass spectrum (m/e): 291(M+1), 128 and 99.

EXAMPLE 7

In 100 ml of ethanol were added 2.77 g of 1-(5-isoquinolinesulfonyl)piperazine, i.e., Compound (35), 1.66 g of anhydrous potassium carbonate and 5.45 g of ethyl bromide, and the reaction was carried out at an external temperature of 70° C. for 24 hours. After the reaction solution was filtered, the filtrate was condensed and the residue was dissolved in 50 ml of chloroform, and the solution was extracted twice with a 2N aqueous hydrochloric acid solution. The aqueous hydrochloric acid layer was rendered alkaline, extracted twice with 50 ml of chloroform, and the chloroform layer extracted was washed with water and dried with anhydrous magnesium sulfate. After the chloroform was distilled therefrom, the residue obtained was subjected to a silica gel column chromatography (silica gel: 100 g; solvent: 2% methanol-chloroform) to give 2.26 g of 1-(5-isoquinolinesulfonyl)-4-ethylpiperazine, i.e., Compound (42) in a yield of 74%.

Melting point (the dihydrochloride recrystallized from ethanol): 221° C.

Mass spectrum (m/e): 305(M+), 290(M-15), 277, 128 and 113.

NMR spectrum (CDCl$_3$, δ): 0.9(3H, t, CH$_3$), 2.2~2.8(6H, m, 3×CH$_2$), 2.9~3.4(4H, m, 2×C$\underline{H}_2$), 7.5~8.9(5H, m) and 9.3(1H, s).

IR absorption spectrum ($\nu_{max}{}^{cap}$, cm$^{-1}$): 1610, 1350, 1340 and 1140.

EXAMPLE 8

The same procedures as in Example 7 were repeated except that 3.7 g of propyl bromide was employed instead of the 5.45 g of ethyl bromide. As a result there was obtained 1.53 g of 1-(5-isoquinolinesulfonyl)-4-propylpiperazine, i.e., Compound (44) in a yield of 48%.

Melting point (the dihydrochloride recrystallized from ethanol): 214° C.

Mass spectrum (m/e): 319(M+), 290(M-29), 127 and 88.

NMR spectrum (CDCl$_3$, δ): 0.8(3H, t, CH$_3$), 1.0~1.7(2H, m, 1×CH$_2$), 2.0~2.7(6H, m, 3×NC$\underline{H}_2$), 3.0~3.3(4H, m, 2×$\overline{N}$C$\underline{H}_2$), 7.5~8.7(5H, m) and 9.2(1H, s).

IR absorption spectrum ($\nu_{max}{}^{cap}$, cm$^{-1}$): 1607, 1350, 1260, 1165 and 1140.

EXAMPLE 9

In 30 ml of chloroform were added 1.42 g of 1-isobutylpiperazine and 2.76 g of potassium carbonate, and to the mixture was added dropwise 50 ml of a chloroform solution containing 2.28 g of 5-isoquinolinesulfonyl chloride under cooling with ice. After the dropwise addition of the chloroform solution, the mixed solution thus obtained was stirred at a temperature of 15° C. to 25° C. for two hours, and then the reaction solution was washed with 20 ml of a 1N aqueous sodium hydroxide solution and extracted twice with a 5N aqueous hydrochloric acid solution. The aqueous hydrochloric acid layer was rendered alkaline extracted three time with 30 ml of chloroform, and the chloroform layer extracted was washed with water and dried with anhydrous magnesium sulfate. After the chloroform was distilled therefrom under reduced pressure, the residue obtained was subjected to a silica gel column chromatography (silica gel; 100 g; solvent: 2% methanol-chloroform) to give 2.60 g of 1-(5-isoquinolinesulfonyl)-4-isobutylpiperazine, i.e., Compound (47) in a yield of 78%.

Melting point (the dihydrochloride recrystallized from ethanol): 234° C.

Mass spectrum (m/e): 333(M+), 290(M-C$_3$H$_7$), 141 and 128.

NMR spectrum (CDCl$_3$, δ): 0.8(6H, d, 2×CH$_3$), 1.2~2.0(1H, m, CH), 2.0~3.3(10H, 5×NC$\underline{H}_2$), 7.6~8.8(5H) and 9.3(1H, s).

IR absorption spectrum ($\nu_{max},{}^{cap}$ cm$^{-1}$): 3430, 1620, 1350, 1340, 1170 and 1145.

The same procedures as described above were repeated using the compounds of Formula (III) as set forth in Table 5-1 under the reaction conditions as set forth in Table 5-1, and there were obtained 1-(5-isoquinolinesulfonyl)-4-n-hexylpiperazine, i.e., Compound (51); 1-(5-isoquinolinesulfonyl)-phenylpiperazine, i.e., Compound (55); 1-(5-isoquinolinesulfonyl)-4-phenethylpiperazine, i.e., Compound (57); 1-(5-isoquinolinesulfonyl)-4-cinnamylpiperazine, i.e., Compound (59); and 1-(5-isoquinolinesulfonyl)-4-(2-ethoxy-4-phenylethyl)piperazine, i.e., Compound (63). The results and the analytical values of these compounds are shown in Table 5-2.

TABLE 5-1

| Run No. | (structure with SO$_2$Cl) (g) | HN⟩N—R$_6$ (g) | K$_2$CO$_3$ (g) | Reaction Temperature (°C.) | Reaction Time (hour) |
|---|---|---|---|---|---|
| 1 | 2.28 | 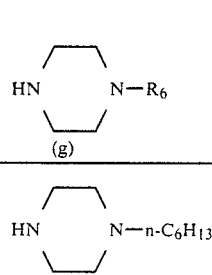 HN⟩N—n-C$_6$H$_{13}$ | 1.70 | 2.76 | 15~25 | 2 |
| 2 | " | 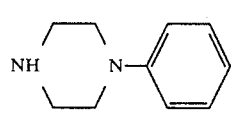 NH⟩N—⟨phenyl⟩ | 1.62 | " | " | " |
| 3 | " | 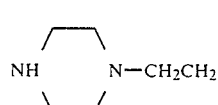 NH⟩N—CH$_2$CH$_2$—⟨phenyl⟩ | 1.9 | " | " | " |
| 4 | " | 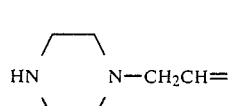 HN⟩N—CH$_2$CH=CH—⟨phenyl⟩ | 2.1 | " | " | " |
| 5 | " | 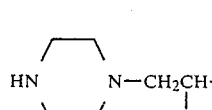 HN⟩N—CH$_2$CH(OC$_2$H$_5$)—⟨phenyl⟩ | 2.34 | " | " | " |

TABLE 5-2

Structure: isoquinoline with SO₂N(piperazine)-N-R₆ at 5-position

| Run No. | Compound No. | R₆ | Yield [g (%)] | Mass Spectrum (m/e) | IR Absorption Spectrum ($v_{max}^{cap}$, cm⁻¹) | NMR Spectrum (CDCl₃) |
|---|---|---|---|---|---|---|
| 1 | (51) | n-C₆H₁₃ | 2.64 (73) | 361, 290, 169, 98 | 1620, 1460, 1350, 1335, 1170, 1140 | 0.6~1.8(11H, 4 × C$\underline{H}_2$ + C$\underline{H}_3$)<br>3.2~3.7(6H, 3 × NC$\underline{H}_2$)<br>3.1~3.5(4H, 2 × NC$\underline{H}_2$)<br>7.4~8.8(5H), 9.3(1H) |
| 2 | (55) | —C₆H₁₁ (cyclohexyl) | 2.44 (69) | 353, 278, 161 | 3400, 1605, 1360, 1170, 1150 | 3.8(8H, 4 × NC$\underline{H}_2$)<br>7.6(5H, C₆$\underline{H}_5$)<br>7.6~9.0(5H), 9.2(1H) |
| 3 | (57) | —CH₂CH₂C₆H₅ | 2.44 (64) | 290 (M—CH₂C₆H₅) | 3400, 1350, 1330, 1155, 950 | 2.5~4.0(12H, 6 × C$\underline{H}_2$)<br>7.3(5H), 7.9~9.0(5H)<br>9.8(1H)<br>(d⁶-dimethyl sulfoxide) |
| 4 | (59) | —CH₂CH=CH—C₆H₅ | 3.58 (91) | 394, 303, 202, 117 | 3400, 1350, 1165, 1140, 935 | 4.0(8H, 4 × NC$\underline{H}_2$)<br>3.9(2H, NC$\underline{H}_2$CH=)<br>6.0~6.5(1H), 6.9(1H)<br>7.3~7.5(5H), 8.0~9.2(5H)<br>9.9(1H)<br>(CD₃OD) |
| 5 | (63) | —CH₂CH(OC₂H₅)C₆H₅ | 3.9 (92) | 381(M-44), 290 | 3400, 1340, 1160, 1135 | 1.2(3H, C$\underline{H}_3$)<br>2.5~4.5(13H, 6 × C$\underline{H}_2$ + C$\underline{H}$)<br>7.2(5H), 7.5~9.0(5H)<br>9.3(1H) |

EXAMPLE 10

In 150 ml of ethanol were added 2.77 g of 1-(5-isoquinolinesulfonyl)piperazine, i.e., Compound (35), 1.0 g of potassium hydroxide and 1.9 g of benzyl chloride, and the mixture was refluxed under heating for five hours. After the ethanol was removed from the reaction solution, 100 ml of chloroform was added to the resulting solution, and the solution obtained was washed with a buffer solution having a pH of 5.5 and extracted twice with 20 ml of a 2N aqueous hydrochloric acid solution. The aqueous hydrochloric acid layer was rendered alkaline, extracted twice with 50 ml of chloroform, and the chloroform layer extracted was washed with water and dried with anhydrous magnesium sulfate. After the chloroform was distilled therefrom under reduced pressure, 5 ml of a 10N aqueous hydrochloric acid solution was added to the residue and the mixture was condensed to dryness. The crystalline residue thus obtained was recrystallized from ethanol to give 2.9 g of 1-(5-isoquinolinesulfonyl)-4-benzylpiperazine [i.e., Compound (56)] dihydrochloride in a yield of 66%.

Melting point: 230° C.

Mass spectrum (m/e): 361(M+1), 290(M-C₅H₁₁), 169 and 98.

NMR spectrum (d⁶-dimethyl sulfoxide, δ): 3.0~4.0(8H, 4×NC$\underline{H}_2$), 3.3(2H, s, NC$\underline{H}_2$), 7.8~8.8(5H) and 9.3(1$\underline{H}$, s).

IR absorption spectrum ($v_{max}^{KBr}$ cm⁻¹): 3550, 3450, 1360 and 1165.

EXAMPLE 11

In 50 ml of chloroform were added 2.77 g of 1-(5-isoquinolinesulfonyl)piperazine, i.e., Compound 35 and 1.54 g of anhydrous potassium carbonate, and to the mixture was added dropwise 1.70 g of benzoyl chloride under cooling with ice, and the mixture was stirred at a temperature of 15° C. to 20° C. for three hours. The reaction solution was washed with a 1N aqueous sodium hydroxide solution, then with water and dried with anhydrous magnesium sulfate. After the chloroform was distilled therefrom, the residue thus obtained was subjected to a silica gel column chromatography (silica gel: 70 g; solvent: chloroform) to give 2.7 g of 1-(5-isoquinolinesulfonyl)-4-benzoylpiperazine, i.e., Compound (58) in a yield of 71%.

Melting point (the hydrochloride): 217° C.

Mass spectrum (m/e): 381(M+), 318, 276 and 289.

NMR spectrum (CDCl₃, δ): 3.1~3.9(8H, 4×C$\underline{H}_2$), 7.2(5H), 7.5~8.5(5H) and 9.3(1H).

IR absorption spectrum ($\nu_{max}^{cap}$ cm$^{-1}$): 1690, 1370 and 1160.

The same procedures as described above were repeated using the compounds of the formula, R$_6$-W under the reaction conditions as set forth in Table 6-1, and there were obtained 1-(5-isoquinolinesulfonyl)-4-cinnamoylpiperazine, i.e., Compound (60) and 1-(5-isoquinolinesulfonyl)-4-furoylpiperazine, i.e., Compound (61). The results and the analytical values of these compounds are shown in Table 6-2.

1.38 g of 1-(5-isoquinolinesulfonyl)-2,5-dimethylpiperazine, Compound (40) in a yield of 59%.

Mass spectrum (m/e): 305, 277, 249, 192 and 128.

NMR spectrum (CDCl$_3$): 0.8~1.3(6H, 2×C$\underline{H}_3$), 1.7(1H, N$\underline{H}$), 2.3~4.2 (6H, 2×C$\underline{H}_2$+×C$\underline{H}$), 7.6(1$\underline{H}$), 8.0~8.8(4$\underline{H}$) and 9.3(1H).

The same procedures as described above were repeated using the compounds of Formula (III) as set forth in Table 7-1 under the reaction conditions as set forth in Table 7-1, and there were obtained 1-(5-

TABLE 6-1

| Run No. | (g) | R$_6$-W (g) | K$_2$CO$_3$ (g) | Reaction Temperature (°C.) | Reaction Time (hour) |
|---|---|---|---|---|---|
| 1 | 2.77 | Ph-CH=CHCOCl | 2.0 | 1.54 | 15~20 | 3 |
| 2 | " | furyl-COCl | | 1.58 | " | " | " |

TABLE 6-2

| Run No. | Compound No. | R$_6$ | Yield [g (%)] | Mass Spectrum (m/e) | IR Absorption Spectrum ($\nu_{max}^{cap}$ cm$^{-1}$) | NMR Spectrum (CDCl$_3$) |
|---|---|---|---|---|---|---|
| 1 | 60 | Ph-CH=CH-C(O)- | 3.26 (80) | 407, 344 277, 215 | 3400, 1645 1600, 1360 1165 | 3.2~3.8(8H, 4 × C$\underline{H}_2$) 6.7~7.5(2H, 2 × C$\underline{H}$) 7.3(5H), 7.9~9.2(5H) 10.0(1H) |
| 2 | 61 | furyl-C(O)- | 3.26 (88) | 371 | 3400, 1620 1490, 1335 1170, 1150 | 3.0~4.0(8H, 4 × C$\underline{H}_2$) 6.4(1H), 6.95(1H) 7.4(1H), 7.4~8.8(5H) 9.3(1H) |

EXAMPLE 12

In 30 ml of methylene chloride were dissolved 1.75 g of 2,5-dimethylpiperazine and 1.53 g of triethylamine, and to the solution was added dropwise 20 ml of a methylene chloride solution containing 1.73 g of 5-isoquinolinesulfonyl chloride under cooling with ice. After the dropwise addition of the methylene chloride solution, the mixed solution obtained was stirred at a temperature of 5° C. to 10° C. for three hours, and then the reaction mixture solution was washed with water and dried with anhydrous magnesium sulfate. After the methylene chloride was distilled therefrom, the residue obtained was subjected to an alumina column chromatography (alumina: 50 g; solvent: chloroform) to give isoquinolinesulfonyl)-3-methylpiperazine, i.e., Compound (37); 1-(5-isoquinolinesulfonyl)-3,5-dimethylpiperazine, i.e., Compound (39); 1-(5-isoquinolinesulfonyl)-2,3-dimethylpiperazine, i.e., Compound (41); 1-(5-isoquinolinesulfonyl)-3-ethylpiperazine, i.e., Compound (43); 1-(5-isoquinolinesulfonyl)-3-isopropylpiperazine, i.e., Compound (45); 1-(5-isoquinolinesulfonyl)-3-isobutylpiperazine, i.e., Compound (46); 1-(5-isoquinolinesulfonyl)-2,5-diethylpiperazine, i.e., Compound (48); 1-(5-isoquinolinesulfonyl)-2-methyl-5-isobutylpiperazine, i.e., Compound (49); 1-(5-isoquinolinesulfonyl)-2-methyl-5-benzylpiperazine, i.e., Compound (50); 1-(5-isoquinolinesulfonyl)-3-phenylpiperazine, i.e., Compound (53); 1-(5-isoquinolinesulfonyl)-3-benzylpiperazine, i.e., Compound (54); and 1-(5-isoquinolinesulfonyl)-3,3-dimethylpiperazine, i.e., Compound (68). The results and the analytical values of these compounds are shown in Table 7-2.

TABLE 7-1

| Run No. | 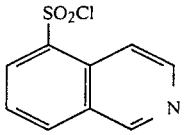 SO₂Cl-isoquinoline (g) | 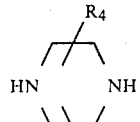 piperazine with R₄, R₅ (g) | N(C₂H₅)₃ (g) | Reaction Temperature (°C.) | Reaction Time (hour) |
|---|---|---|---|---|---|
| 1 | 1.73 | 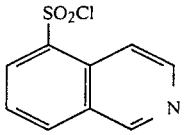 R₄=CH₃ | 1.52 | 1.53 | 2~10 | 2 |
| 2 | " | 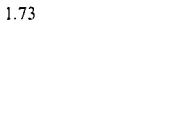 R₄=CH₃, R₅=CH₃ | 1.73 | " | " | " |
| 3 | 1.0 |  R₄=CH₃, R₅=CH₃ (both on same C) | 1.25 | 1.1 | 15~25 | 1 |
| 4 | 1.14 |  R₄=C₂H₅ | 1.14 | 1.0 | " | 10 |
| 5 | " |  R₄=i-C₃H₇ | 1.28 | " | " | 18 |
| 6 | " |  R₄=i-C₄H₉ | 1.42 | " | " | " |
| 7 | 1.73 |  R₄=C₂H₅, R₅=C₂H₅ | 2.28 | 1.53 | " | " |
| 8 | 1.0 | 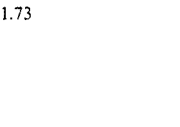 R₄=CH₃, R₅=i-C₄H₉ | 3.43 | 2.3 | 38 | 20 |

TABLE 7-1-continued

| Run No. | SO₂Cl-isoquinoline (g) | Diamine (R₄/R₅) (g) | N(C₂H₅)₃ (g) | Reaction Temperature (°C.) | Reaction Time (hour) |
|---|---|---|---|---|---|
| 9 | " | H₃C— on piperazine with CH₂C₆H₅ | 4.17 | " | " | " |
| 10 | " | C₆H₅— piperazine | 3.56 | " | " | " |
| 11 | " | CH₂C₆H₅— piperazine | 3.90 | " | " | " |
| 12 | 1.14 | gem-di-CH₃ piperazine | 1.14 | 1.0 | 15~25 | " |

TABLE 7-2

| Run No. | Compound No. | R₄/R₅ | Yield [g (%)] | Mass Spectrum (m/e) | IR Absorption Spectrum ($\nu_{max}^{cap}$, cm⁻¹) | NMR Spectrum (CDCl₃) |
|---|---|---|---|---|---|---|
| 1 | (37) | CH₃ (piperazine, one N connected) | 1.60 (88) | 276, 206, 162, 148 | 3300, 3000, 2950, 2850, 1610, 1560, 1480, 1360, 1330, 1160, 1140, 1070, 1040 | 0.95(3H, CH₃), 1.6(1H, NH), 1.8~3.2(5H), 3.65(2H), 7.6(1H), 8.1~8.7(4H), 9.3(1H) |
| 2 | (39) | 2,5-di-CH₃ piperazine | 2.14 (92) | 305, 278, 264, 249, 192, 128, 114 | 3350, 2920, 2850, 1450, 1370, 1330, 1155, 1140 | 1.0(6H, 2 × CH₃), 2.1(2H), 2.5~3.3(2H), 3.6~4.0(2H), 4.3(1H, NH), 7.8(1H), 8.1~8.8(4H), 9.4(1H) |

TABLE 7-2-continued

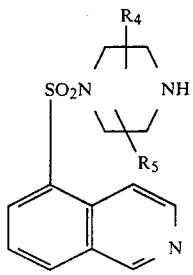

| Run No. | Compound No. | R₅ structure | Yield [g (%)] | Mass Spectrum (m/e) | IR Absorption Spectrum ($\nu_{max}^{cap}$, cm⁻¹) | NMR Spectrum (CDCl₃) |
|---|---|---|---|---|---|---|
| 3 | (41) | 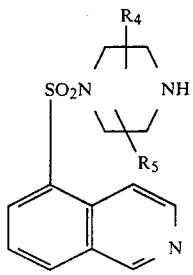 | 1.0 (75) | 305, 277 249, 192 128 | 3400, 2920 2850, 1610 1360, 1330 1160, 1140 | 0.9~1.3(6H, 2 × C$\underline{H}$₃) 1.6(1H, N$\underline{H}$), 2.6~4.3(6H) 7.6(1H), 8.1~8.8(4H) 9.3(1H) |
| 4 | (43) | 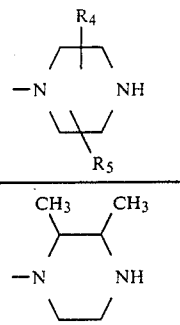 | 1.07 (70) | 305, 206 192, 128 114 | 3400, 2950 2800, 1600 1360, 1340 1160, 1140 | 1.0(3H, C$\underline{H}$₃), 1.4(2H) 2.1(1H, N$\underline{H}$), 1.8~3.0(5H) 3.6(2H), 7.6(1H) 8.0~8.6(4H), 9.3(1H) |
| 5 | (45) | 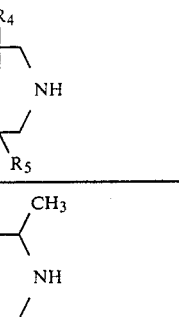 | 1.02 (64) | 319, 276 221, 128 | 3400, 1610 1480, 1370 1335, 1160 1130 | 0.7~1.3(7H, C₃$\underline{H}$₇), 2.1(1H, N$\underline{H}$) 1.8~3.5(5H), 3.7(2H) 7.6(1H), 8.1~8.8(4H) 9.3(1H) |
| 6 | (46) | 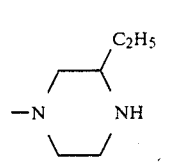 | 1.07 (64) | 333, 221 128 | 3350, 1600 1470, 1360 1330, 1160 1140 | 0.5~1.3(9H, C₄$\underline{H}$₉), 2.7(1H, N$\underline{H}$) 2.0~3.4(5H), 3.75(2H) 7.5(1H), 8.1~8.7(4H), 9.3(1H) |
| 7 | (48) | 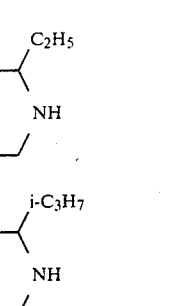 | 1.65 (65) | 333, 265 248, 192 | 3400, 1610 1400, 1360 1340, 1160 1130 | 0.7~1.8(10H, 2 × C₂$\underline{H}$₅), 1.7(1H) 2.3~4.3(6H), 7.6(1H) 8.0~8.7(4H), 9.3(1H) |
| 8 | (49) | 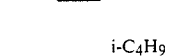 | 0.88 (58) | 347, 220 192, 128 | 3400, 1610 1450, 1360 1340, 1160 1130 | 0.7~1.8(12H, C₄$\underline{H}$₉ + C$\underline{H}$₃) 1.8(1H), 2.0~4.1(6H), 7.7(1H) 8.1~8.8(4H), 9.3(1H) |
| 9 | (50) | 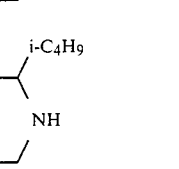 | 1.25 (75) | 381, 291 220, 128 | 3350, 1600 1500, 1355 1340, 1160 1130 | 1.0(3H, C$\underline{H}$₃), 1.6(1H, N$\underline{H}$) 2.0~4.3(8H), 7.1(5H) 7.6(1H), 8.0~8.6(4H) 9.3(1H) |

TABLE 7-2-continued $$\text{Structure: } SO_2N(R_4)(CH_2C(R_5)NH) \text{ on isoquinoline}$$

| Run No. | Compound No. | $-N\underset{\diagdown}{\overset{R_4}{\diagup}}NH$ with $R_5$ | Yield [g (%)] | Mass Spectrum (m/e) | IR Absorption Spectrum ($\nu_{max}^{cap}$, cm$^{-1}$) | NMR Spectrum (CDCl$_3$) |
|---|---|---|---|---|---|---|
| 10 | (53) | piperazine with -CH(C$_6$H$_5$)- substituent | 1.23 (79) | 353, 312, 278, 235, 192, 167 | 3300, 1600, 1510, 1360, 1335, 1160, 1140 | 1.6(1H), 1.8~3.2(5H), 3.65(2H), 7.2(5H), 7.6(1H), 8.1~8.7(4H), 9.3(1H) |
| 11 | (54) | piperazine with -CH(CH$_2$C$_6$H$_5$)- substituent | 1.13 (70) | 367, 276, 220, 148, 128 | 3400, 1600, 1500, 1360, 1340, 1160, 1140 | 1.0~1.5(2H), 1.9(1H), 1.9~3.2(5H), 3.7(2H), 7.2(5H), 7.6(1H), 8.1~8.7(4H), 9.3(1H) |
| 12 | (68) | piperazine with -C(CH$_3$)$_2$- substituent | 0.96 (63) | 305, 290, 276, 191, 129 | 3300, 3000, 2950, 1620, 1560, 1370, 1160, 1140 | 1.2(6H, 2 × C$\underline{H}_3$), 1.3~2.1(1H, N$\underline{H}$), 2.6~3.4(6H, 3 × C$\underline{H}_2$), 7.6(1H), 8.0~8.7(4H), 9.3(1H) |

EXAMPLE 13

In 50 ml of chloroform were dissolved 4.68 g of 1-benzyloxycarbonyl-3-methylpiperazine and 1.01 g of triethylamine, and to the solution was added dropwise 20 ml of a chloroform solution containing 4.55 g of 5-isoquinolinesulfonyl chloride, and the mixed solution was stirred at a temperature of 20° C. to 25° C. for 20 hours. The reaction solution obtained was washed with a saturated aqueous sodium hydrogencarbonate solution then with a saturated aqueous ammonium chloride solution, dried with anhydrous magnesium sulfate and concentrated to dryness under reduced pressure to 8.1 g of 1-(5-isoquinolinesulfonyl)-4-benzyloxycarbonyl-2-methylpiperazine as a yellowish white oily substance.

NMR spectrum (CDCl$_3$): 1.0(3H, d, C$\underline{H}_3$), 2.5~4.3(7H), 5.0(2H, S,

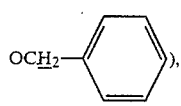

OC$\underline{H}_2$—C$_6$H$_5$), 7.25(5H, S, C$_6\underline{H}_5$), 7.55(1H), 8.0~8.7(4H) and 9.2(1H).

IR absorption spectrum ($\nu_{max}^{cap}$ cm$^{-1}$): 1700, 1360 and 1130.

To 1.65 g of 1-(5-isoquinolinesulfonyl)-4-benzyloxycarbonyl-2-methylpiperazine as obtained above was added 5 ml of 25% hydrobromic acid-acetic acid, and the mixture was stirred at 20° C. for five hours. To the reaction solution was added 30 ml of ethyl ether, and the crystals precipitated were separated by filtration. The crystals thus obtained were dissolved in 20 ml of water and washed with chloroform. Then the pH of the aqueous layer was adjusted to 9 with a 1N aqueous sodium hydroxide solution, extracted with chloroform, and the chloroform layer was washed with water and dried with anhydrous magnesium sulfate. Then the chloroform was distilled therefrom under reduced pressure to give 1.05 g of 1-(5-isoquinolinesulfonyl)-2-methylpiperazine, i.e., Compound (38) in a yield of 93%.

Mass spectrum (m/e): 291, 277, 249, 192, 129 and 128.

NMR spectrum (CDCl$_3$): 1.3(6H, d, 2×CH$_3$), 1.9(1H, N$\underline{H}$), 2.2~3.1(4H), 3.1~4.0(2H), 4.2(1$\overline{H}$), 7.7(1H), 8.1~8.8(4H) and 9.3(1H).

IR spectrum ($\nu_{max}^{cap}$ cm$^{-1}$): 3330, 2940, 2870, 2830, 1607, 1370, 1320, 1160, 1135, 990 and 760.

EXAMPLE 14

In 40 ml of chloroform were dissolved 2.23 g of 2-benzyloxycarbonyl-1-methylethylamine and 1.2 g of triethylamine, and to the solution was added dropwise 20 ml of a chloroform solution containing 2.28 g of 5-isoquinolinesulfonyl chloride under cooling with ice. After the dropwise addition of the chloroform solution, the mixed solution was stirred at a temperature of 20° C. to 25° C. for two hours. The reaction solution obtained was washed with a saturated aqueous hydrogencarbonate solution, then with water, dried with anhydrous magnesium sulfate and then the chloroform was distilled therefrom under reduced pressure to give 3.55 g of N-(2-benzyloxycarbonylamino-1-methylethyl)-5-isoquinolinesulfonamide in a yield of 89%.

NMR spectrum (CDCl$_3$): 0.95(3H, C$\underline{H}_3$), 2.5~4.5(3H), 5.0(2H,

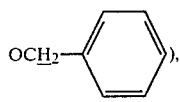

6.6(1H), 7.2(5H), 7.6(1H), 8.0~8.6(4H) and 9.3(1H).

IR absorption spectrum ($\nu_{max},^{cap}$ cm$^{-1}$): 3350, 1700, 1330 and 1160.

To 2.0 g of N-(2-benzyloxycarbonylamino-1-methylethyl)-5-isoquinolinesulfonamide as obtained above was added 5 ml of 25% hydrobromic acid-acetic acid, and the mixture was stirred at a temperature of 20° C. to 25° C. for 20 hours. To the reaction solution was added 30 ml of ethyl ether, and the crystals precipitated were separated by filtration. The crystals thus obtained were dissolved in 20 ml of water, washed with chloroform, rendered alkaline with a 1N sodium hydroxide solution and extracted with chloroform. The chloroform layer was washed with water, dried with anhydrous magnesium sulfate and the chloroform was distilled under reduced pressure to give 1.2 g of N-(2-amino-1-methylethyl)-5-isoquinolinesulfonamide, i.e., Compound (6) in a yield of 90%.

Mass spectrum (m/e): 265, 240, 221, 192 and 128.

NMR spectrum (CDCl$_3$): 1.1(3H), 1.7(2H), 2.6(2H), 3.7(1H), 6.5(1H), 7.6(1H), 8.0~8.7(4H) and 9.3(1H).

IR absorption spectrum ($\nu_{max},^{cap}$ cm$^{-1}$): 3400, 2900, 1610, 1460, 1330, 1160 and 1140.

The same procedures as described above were repeated using the compounds of Formula (III) as set forth in Table 8-1 under the reaction conditions as set forth in Table 8-1 and Table 8-2, and there were obtained N-(1-aminomethylpropyl)-5-isoquinolinesulfonamide, i.e., Compound (7); N-(1-aminomethylpentyl)-5-isoquinolinesulfonamide, i.e., Compound (8); and N-(2-amino-1-phenylethyl)-5-isoquinolinesulfonamide, i.e., Compound (12). The analytical values of these compounds thus obtained are shown in Table 8-3.

TABLE 8-1

| Run No. | SO$_2$Cl-isoquinoline (g) | R$_1$ in NH$_2$CHCH$_2$NH—Z | (g) | N(C$_2$H$_5$)$_3$ (g) | Reaction Temperature (°C.) | Reaction Time (hour) | Yield [g | (%)] | IR Absorption Spectrum ($\nu_{max}^{cap}$ cm$^{-1}$) |
|---|---|---|---|---|---|---|---|---|---|
| 1-1 | 2.28 | C$_2$H$_5$ | 2.4 | 1.2 | 20~25 | 4 | 3.5 | (85) | 1710, 1330, 1160 |
| 2-1 | " | n-C$_4$H$_9$ | 2.8 | " | " | " | 3.1 | (70) | 1710, 1340, 1160 |
| 3-1 | " | phenyl | 3.0 | " | " | " | 3.4 | (74) | 1710, 1330, 1160 |

TABLE 8-2

| Run No. | R$_1$ | (g) | 25% HBr—CH$_3$COOH (ml) | Reaction Temperature (°C.) | Reaction Time (hour) | Product Compound No. | Yield [g | (%)] |
|---|---|---|---|---|---|---|---|---|
| 1-2 | C$_2$H$_5$ | 1.5 | 5 | 20~25 | 12 | (7) | 0.90 | (89) |
| 2-2 | n-C$_4$H$_9$ | " | " | " | " | (8) | 0.92 | (88) |
| 3-2 | phenyl | " | " | " | 18 | (12) | 0.74 | (70) |

TABLE 8-2-continued

SO₂NHCHCH₂NH—Z with R₁ substituent on isoquinoline ring

| Run No. | R₁ | 25% HBr—CH₃COOH (g) | CH₃COOH (ml) | Reaction Temperature (°C.) | Reaction Time (hour) | Product Compound No. | Yield [g (%)] |
|---|---|---|---|---|---|---|---|

Reaction scheme: SO₂Cl-isoquinoline + NH₂CHR₁CH₂NH—Z → SO₂NHCHR₁CH₂NH—Z-isoquinoline  (Z = —COOCH₂—C₆H₅)

TABLE 8-3

SO₂NHCHCH₂NH₂ with R₁ substituent on isoquinoline ring

| Run No. | Compound No. | R₁ | Mass Spectrum (m/e) | IR Absorption Spectrum ($\nu_{max}^{cap}$ cm$^{-1}$) | NMR Spectrum (CDCl₃) |
|---|---|---|---|---|---|
| 1 | (7) | C₂H₅ | 279, 249, 221, 192, 128 | 3400, 2900, 1460, 1360, 1160, 1140 | 0.8(3H, CH₃), 1.0~1.7(2H), 1.9(2H, NH₂), 2.5~4.0(3H), 6.7(1H), 7.6~8.8(5H), 9.3(1H) |
| 2 | (8) | n-C₄H₉ | 307, 277, 221, 192, 128 | 3350, 2900, 1370, 1160, 1130 | 0.7~2.0(9H), 2.1(2H, NH₂), 2.5~3.8(3H), 7.0(1H), 7.6~8.8(5H), 9.3(1H) |
| 3 | (12) | phenyl (C₆H₅) | 327, 297, 192, 128 | 3350, 1610, 1350, 1160, 1140 | 1.7(2H, NH₂), 2.5~4.4(3H), 6.6(1H), 7.1(5H), 7.7~8.8(5H), 9.3(1H) |

EXAMPLE 15

In 50 ml of chloroform were dissolved 2.0 g of 2-acetamidopropylamine and 2.6 g of triethylamine, and to the solution was added dropwise 50 ml of a chloroform solution containing 3.28 g of 5-isoquinolinesulfonyl chloride under cooling with ice. Then the mixed solution was stirred at a temperature of 15° C. to 25° C. for two hours, and the reaction solution was washed with water, dried with anhydrous magnesium sulfate and the chloroform was distilled therefrom under reduced pressure to give 3.67 g of N-(2-acetamidopropyl)-5-isoquinolinesulfonamide in a yield of 83%.

NMR spectrum (CDCl₃): 1.0(3H, d, CH₃), 2.2(3H, COCH₃), 2.6~3.8(3H), 5.5~7.0(2H), 7.6(1H), 8.0~8.7(4H) and 9.3(1H).

IR absorption spectrum ($\nu_{max}^{cap}$ cm$^{-1}$) 3300, 1670, 1365, 1150, 1130.

The reaction mixture of 3.0 g of the N-(2-acetamidopropyl)-5-isoquinolinesulfonamide as obtained above and 50 ml of 10% hydrochloric acid was stirred at a temperature of 90° C. to 100° C. for 36 hours. Then the reaction solution was washed with chloroform, rendered alkaline with 1N sodium hydroxide and extracted with chloroform. The chloroform layer was washed with water, dried with anhydrous magnesium sulfate, and the chloroform was distilled therefrom under reduced pressure. The residue thus obtained was subjected to an alumina column chromatography (alumina: 70 g; solvent: chloroform) to give 1.14 g of N-(2-aminopropyl)-5-isoquinolinesulfonamide, i.e., Compound (9) in a yield of 44%.

Mass spectrum (m/e): 265, 222, 193, 129 and 128.

NMR spectrum (CDCl₃): 1.0(3H), 1.7(2H), 2.9~4.0(3H), 6.8(1H), 7.5(1H), 8.1~8.6(4H) and 9.3(1H).

IR absorption spectrum ($\nu_{max}^{cap}$ cm$^{-1}$): 3400, 1610, 1460, 1370, 1150 and 1130.

The same procedures as described above were repeated using the compounds of Formula (IV) as set forth in Table 9-1 under the reaction conditions as set forth in Table 9-1 and Table 9-2, and there were obtained N-(2-amino-3-methylbutyl)-5-isoquinolinesulfonamide, i.e., Compound (11) and N-(2-amino-2-phenylethyl)-5-isoquinolinesulfonamide, i.e., Compound (13). The analytical values of these compounds are shown in Table 9-3.

TABLE 9-1

Product structure: 5-isoquinolinesulfonamide with SO₂NHCH₂CH(R₁)NH—COCH₃

Starting material: 5-isoquinolinesulfonyl chloride (SO₂Cl)

Reactant: $H_2NCH_2CH(R_1)NH-COCH_3$

| Run No. | (g) | R₁ | (g) | $N(C_2H_5)_3$ (g) | Reaction Temperature (°C.) | Reaction Time (hour) | Yield [g | (%)] | IR Absorption Spectrum ($\nu_{max}^{cap}$, cm$^{-1}$) |
|---|---|---|---|---|---|---|---|---|---|
| 1-1 | 2.28 | i-C₃H₇ | 2.16 | 1.6 | 15~20 | 0.5 | 2.31 | (69) | 1665, 1330, 1160 |
| 2-1 | " | phenyl (–C₆H₅) | 2.67 | " | " | 1 | 2.77 | (75) | 1660, 1330, 1160 |

TABLE 9-2

Substrate: 5-isoquinoline-SO₂NHCH₂CH(R₁)NH—COCH₃

| Run No. | R₁ | (g) | 10% HCl (ml) | Reaction Temperature (°C.) | Reaction Time (hour) | Product Compound No. | Yield [g | (%)] |
|---|---|---|---|---|---|---|---|---|
| 1-2 | i-C₃H₇ | 1.34 | 30 | 100 | 35 | (11) | 0.60 | (51) |
| 2-2 | phenyl (–C₆H₅) | 1.11 | " | " | 30 | (13) | 0.38 | (39) |

Reaction scheme:

5-isoquinoline-SO₂Cl + $NH_2CH_2CH(R_1)NH-COCH_3$ → 5-isoquinoline-SO₂NHCH₂CH(R₁)NH—COCH₃

TABLE 9-3

Product: 5-isoquinoline-SO₂NHCH₂CH(R₁)NH₂

| Run No. | Compound No. | R₁ | Mass Spectrum (m/e) | IR Absorption Spectrum ($\nu_{max}^{cap}$, cm$^{-1}$) | NMR Spectrum (CDCl₃) |
|---|---|---|---|---|---|
| 1 | (11) | i-C₃H₇ | 221, 192, 148, 128 | 3450, 1600, 1460, 1330, 1160, 1140 | 0.9(6H, 2 × C$\underline{H}_3$), 1~1.8(1H) 2.5~3.8(3H), 2.1(2H) 7.6(1H), 8.1~8.9(4H) 9.3(1H) |
| 2 | (13) | phenyl (–C₆H₅) | 221, 192, 148, 128 | 3400, 1610, 1440, 1400, 1330, 1150 | 1.7(2H, NH₂), 2.7~4.0(3H) 6.8(1H), 7.2(5H), 7.6(1H) 8.0~8.8(4H), 9.3(1H) |

EXAMPLE 16

In 70 ml of methylene chloride were dissolved 3.24 g of 2-(N-methyl-N-benzylamino)ethylamine and 2.0 g of triethylamine, and to the solution was added dropwise 50 ml of a methylene chloride solution containing 3.0 g of 5-isoquinolinesulfonyl chloride under cooling with ice. After the dropwise addition of the methylene chloride solution, the mixed solution was stirred at a temperature of 15° C. to 25° C. for one hour, and then the reaction solution was washed with water and extracted with a 10% aqueous hydrochloric acid solution. The aqueous layer was washed with chloroform, rendered alkaline with a 1N aqueous sodium hydroxide solution, extracted with chloroform, and then the chloroform layer was washed with water, dried with anhydrous magnesium sulfate and the chloroform was distilled therefrom under reduced pressure. The residue thus obtained was subjected to a silica gel column chromatography (silica gel: 100 g; solvent: chloroform) to give 3.84 g of N-[2-(N-methyl-N-benzylamino)ethyl]-5-isoquinolinesulfonamide, i.e., Compound (65) in a yield of 84%.

Mass spectrum (m/e): 355, 340, 264, 221 and 128.

NMR spectrum (CDCl$_3$): 1.9(3H, NC$\underline{H}_3$), 2.3~2.7(2H), 3.0~3.3(2H), 3.5(2H, C$\underline{H}_2$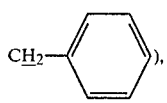), 6.8(1H), 7.2(5H), 7.6(1H), 8.0~8.5(4H) and 9.3(1H).

IR absorption spectrum ($\nu_{max.}^{cap}$ cm$^{-1}$): 3050, 2950, 1620, 1450, 1330, 1155 and 1135.

The same procedures as described above were repeated using the compound of Formula (III) as set forth in Table 10-1 under the reaction conditions as set forth in Table 10-1, and there was obtained N-[2-(N-isopropyl-N-benzylamino)ethyl]-5-isoquinolinesulfonamide, i.e., Compound (67). The analytical values of this compound are shown in Table 10-2.

TABLE 10-1

| (structure with SO$_2$Cl) (g) | H$_2$N(CH$_2$)$_2$N(i-C$_3$H$_7$)(CH$_2$C$_6$H$_5$) (g) | N(C$_2$H$_5$)$_3$ (g) | Reaction Temperature (°C.) | Reaction Time (hour) | Product Compound (67) Yield [g (%)] |
|---|---|---|---|---|---|
| 4.55 | 3.84 | 2.2 | 15~25 | 1 | 5.44 (71) |

TABLE 10-2

| Product Compound (67) | Mass Spectrum (m/e) | IR Absorption Spectrum ($\nu_{max.}^{cap}$ cm$^{-1}$) | NMR Spectrum (CDCl$_3$) |
|---|---|---|---|
| (structure) | 383, 340, 221, 128 | 2950, 1610, 1450, 1335, 1160, 1140 | 0.9(6H, 2 × C$\underline{H}_3$), 2.5~2.8(3H), 3.3(2H), 3.7(2H, C$\underline{H}_2$—phenyl), 6.8(1H), 7.2(5H), 7.6~8.5(5H), 9.3(1H) |

EXAMPLE 17

In 100 ml of ethanol was dissolved 2.0 g of N-[2-(N-methyl-N-benzylamino)ethyl]-5-isoquinolinesulfonamide, i.e., Compound (65) as obtained in Example 16, and to the solution was added 0.2 g of 10% palladium-carbon. Then the solution was vigorously stirred at a temperature of 20° C. to 25° C. in a hydrogen stream of 2.0 to 2.5 atm. for 5 hours. After the palladium-carbon was separated from the reaction solution by filtration, the reaction solution was concentrated to dryness to give 0.95 g of N-(2-methylaminoethyl)-5-isoquinolinesulfonamide, i.e., Compound (14) in a yield of 64%.

Mass spectrum (m/e): 265, 250, 221 and 128.

NMR spectrum (CDCl$_3$): 1.7(1H, N$\underline{H}$), 2.9(3H, C$\underline{H}_3$), 2.5~3.1(2H), 3.1~3.5(2H), 7.0(1H), 7.6(1H), 8.1~8.5(4H) and 9.3(1H).

IR absorption spectrum ($\nu_{max.}^{cap}$ cm$^{-1}$): 3400, 1610, 1350, 1330, 1160 and 1140.

The same procedures as described above were repeated using Compound (67) under the reaction conditions as set forth in Table 11-1, and there was obtained N-(2-isopropylaminoethyl)-5-isoquinolinesulfonamide, i.e., Compound (16). The analytical values of this compound are shown in Table 11-2.

TABLE 11-1

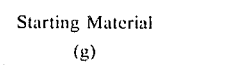

| Starting Material (g) | 10% Pd—C (g) | Hydrogen Pressure (atm.) | Reaction Temperature (°C.) | Reaction Time (hour) | Product Yield [g (%)] |
|---|---|---|---|---|---|
| Compound (67) | 0.15 | 2 | 20~25 | 10 | 0.50 (44) |

TABLE 11-2

| Product Compound (16) | Mass Spectrum (m/e) | IR Absorption Spectrum ($\nu_{max}^{cap}$, cm$^{-1}$) | NMR Spectrum (CDCl$_3$) |
|---|---|---|---|
| SO$_2$NH(CH$_2$)$_2$N(i-C$_3$H$_7$)H on isoquinoline | 293, 263, 221, 143, 128 | 3400, 1600, 1350, 1330, 1160, 1140 | 1.0(6H, 2 × CH$_3$), 2.1(1H, NH), 2.5~2.9(2H), 3.0~3.5(3H), 6.8(1H), 7.6~8.8(5H), 9.3(1H) |

RELAXATION OF MESENTERIC ARTERY

After a home bred rabbit of a Japanese species weighing about 3 Kg was subjected to bloodletting, resulting in death and then to abdominal incision, the mesenteric artery was taken out, cut into helicoids of 2 mm×25 mm and suspended in a 20 ml organ bath filled with a Krebs-Henseleit solution into which a mixed gas of 95% by volume of O$_2$ and 5% by volume of CO$_2$ was introduced and one end of the artery was connected with an isometric transducer. When a load of 1.5 g was applied to the artery, the contraction and the relaxation of the artery were recorded as a weight on the transducer (a product of Nippon Koden K.K., Japan, "FD Pickup TB-912T"). The relaxation of the mesenteric artery was observed by adding the isoquinolinesulfonyl derivatives and their pharmaceutically acceptable acid addition salts of this invention to the mesenteric artery at the condition of about one half of the maximum contraction with KCl at a KCl concentration of 15~20 mM. When the complete relaxation of the mesenteric artery was designated 100%, the concentration of the isoquinolinesulfonyl derivatives and their pharmaceutically acceptable acid addition salts which brought about a relaxation of 50% is shown in Table 12.

TABLE 12

| Compound Nos. | Relaxation of Mesenteric Artery ED$_{50}$ ($\mu$M) | Compound Nos. | Relaxation of Mesenteric Artery ED$_{50}$ ($\mu$M) |
|---|---|---|---|
| (1) | 5 | (34) | 10 |
| (2) | 7 | (35) | 0.6 |
| (3) | 11 | (36) | 7.7 |
| (4) | 10 | (37) | 4.0 |
| (5) | 14 | (38) | 5.0 |
| (6) | 10 | (39) | 9.5 |
| (7) | 21 | (40) | 0.6 |
| (8) | 19 | (41) | 1.5 |
| (9) | 15 | (42) | 18 |
| (11) | 28 | (43) | 6.1 |
| (12) | 18 | (44) | 8.6 |
| (13) | 25 | (45) | 7.5 |
| (14) | 12 | (46) | 6.5 |
| (16) | 10 | (47) | 24 |
| (17) | 10 | (48) | 1.8 |
| (18) | 30 | (49) | 10 |
| (19) | 17 | (50) | 16 |
| (20) | 42 | (51) | 19 |
| (21) | 50 | (53) | 7 |
| (22) | 42 | (54) | 11 |
| (23) | 4.0 | (55) | 9 |
| (24) | 17 | (56) | 23 |
| (25) | 13 | (57) | 12 |
| (26) | 8.8 | (58) | 40 |
| (27) | 21 | (59) | 6.8 |
| (28) | 19 | (60) | 27 |
| (29) | 13 | (61) | 24 |
| (30) | 8.9 | (63) | 13 |
| (31) | 28 | (65) | 13 |
| (32) | 16 | (67) | 18 |
| (33) | 11 | | |

EFFECT ON BLOOD FLOW VOLUME OF FEMORAL AND VERTEBRAL ARTERIES OF DOG

The effect on the vasodilatation of the femoral and vertebral arteries was measured by anesthetizing a dog of mixed breed weighing 8 to 15 Kg by an intravenous administration of 35 mg/Kg of pentabarbital, providing an acute type probe (a product of Nippon Koden K.K., Japan) with the femoral and vertebral arteries, administering the 5-isoquinolinesulfonyl derivatives and their pharmaceutically acceptable acid addition salts to the femoral vein through a polyethylene tube inserted into the femoral vein side chain and measuring the blood flow volume with an electromagnetic blood flowmeter (a product of Nippon Koden K.K., Japan, "MF-27"). The results are shown in Table 13.

TABLE 13

| Compound Nos. | Amount of Intravenous Administration (mg/Kg) | Increased Blood Flow Volume in Femoral Artery (%) | Increased Blood Flow Volume in Vertebral Artery (%) |
|---|---|---|---|
| 1 | 1 | 30 | 45 |
| 3 | 1 | 33 | 36 |
| 19 | 1 | 25 | 20 |
| 25 | 1 | 38 | 29 |
| 33 | 1 | 35 | 37 |
| 35 | 1 | 69 | 98 |
| 36 | 1 | 35 | 63 |
| 37 | 1 | 65 | 90 |
| 40 | 1 | 50 | 110 |
| 46 | 1 | 32 | 55 |
| 51 | 1 | 39 | 68 |
| 59 | 1 | 25 | 49 |

ACUTE TOXICITY

The acute toxicity of the 5-isoquinolinesulfonyl derivatives and their pharmaceutically acceptable acid addition salts were measured by giving male ddY-strain mice an intravenous administration. The results are shown in Table 14.

TABLE 14

| Compound Nos. | LD$_{50}$ (mg/Kg) |
|---|---|
| 1 | 108 |
| 3 | 87 |
| 19 | 180 |
| 25 | 137 |
| 33 | 150 |

TABLE 14-continued

| Compound Nos. | LD$_{50}$ (mg/Kg) |
|---|---|
| 35 | 29 |
| 36 | 94 |
| 37 | 89 |
| 40 | 42 |
| 46 | 130 |
| 51 | 108 |
| 59 | 145 |

While the invention has been described in detail and with reference to specific embodiments thereof, it will be apparent to one skilled in the art that various changes and modifications can be made therein without departing from the spirit and scope thereof.

What is claimed is:

1. A compound of Formula (I):

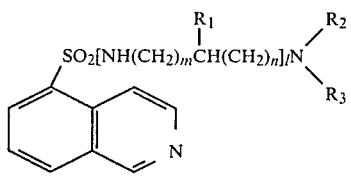

wherein
l is zero or one;
m and n each is zero or an integer of one to nine;
m+n is an integer of at least one;
$R_1$ is a hydrogen atom, a $C_{1-10}$ alkyl group, a $C_{5-6}$ cycloalkyl group or a phenyl group;
$R_2$ and $R_3$ are independently $C_{1-6}$ alkylene groups and linked through an oxygen atom to form a 5- to 7-membered hetrocyclic ring with the adjacent nitrogen atom;
or the pharmaceutically acceptable acid addition salt thereof.

2. The compound of claim 1 wherein l is zero; $R_2$ and $R_3$ are $C_{1-6}$ alkylene groups and linked through an oxygen atom to form a 5- or 7-membered heterocyclic ring together with the adjacent nitrogen atom.

3. The compound of claim 2 wherein $R_2$ and $R_3$ form together with the adjacent nitrogen atom a morpholino group.

4. The compound of claim 1 wherein l is one; m and n each is zero or an integer of one to nine; m+n is an integer of one to nine; $R_1$ is a hydrogen atom, a $C_{1-6}$ alkyl or a phenyl group; and $R_2$ and $R_3$ are independently $C_{1-6}$ alkylene groups and linked through an oxygen atom to form a 5- to 7-membered heterocyclic ring together with the adjacent nitrogen atom.

5. The compound of claim 4 wherein m and n each is zero or an integer of one to nine; m+n is an integer of one to nine; and $R_1$ is a hydrogen atom.

6. The compound of claim 4 wherein m and n each is zero or one; m+n is one; and $R_1$ is a $C_{1-6}$ alkyl group or a phenyl group.

7. The compound of claim 4 wherein m and n each is zero or an integer of one to two; m+n is one or two; and $R_1$ is a hydrogen atom.

8. The compound of claim 4 wherein m and n each is zero or an integer of one to two; m+n is one or two; and $R_2$ and $R_3$ form together with the adjacent nitrogen atom a morpholino group.

* * * * *